United States Patent [19]

Ichijima et al.

[11] Patent Number: 4,698,297

[45] Date of Patent: Oct. 6, 1987

[54] SILVER HALIDE COLOR PHOTOGRAPHIC LIGHT-SENSITIVE MATERIAL

[75] Inventors: Seiji Ichijima; Noboru Sasaki, both of Kanagawa, Japan

[73] Assignee: Fuji Photo Film Co., Ltd., Kanagawa, Japan

[21] Appl. No.: 737,853

[22] Filed: May 28, 1985

[30] Foreign Application Priority Data

May 25, 1984 [JP] Japan ................... 59-106223

[51] Int. Cl.$^4$ .......................... G03C 1/40; G03C 1/06; G03C 1/10; G03C 1/42
[52] U.S. Cl. .................... 430/383; 430/223; 430/226; 430/380; 430/543; 430/544; 430/559; 430/564; 430/566; 430/598; 430/955; 430/957; 430/959
[58] Field of Search ............. 430/957, 955, 542, 598, 430/559, 544, 223, 226, 566, 564, 543, 959, 382, 383, 380

[56] References Cited

U.S. PATENT DOCUMENTS 4,390,618  6/1983  Kobayashi et al. ............. 430/955

Primary Examiner—Richard L. Schilling
Attorney, Agent, or Firm—Sughrue, Mion, Zinn, Macpeak, and Seas

[57] ABSTRACT

A silver halide color photographic light-sensitive material comprising a support having thereon at least one silver halide emulsion layer, the color photographic light-sensitive material containing a compound capable of releasing a group represented by the general formula (I) described below upon the reaction with the oxidation product of a developing agent:

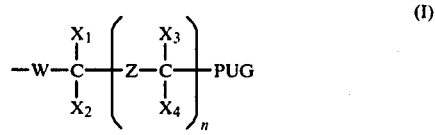

wherein W and Z each represents an oxygen atom, a sulfur atom or a group of

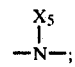

$X_1$, $X_2$, $X_3$, $X_4$ and $X_5$ each represents a hydrogen atom or an organic residue; PUG represents a photographically useful group; n represents 1 or 2; any two of $X_1$, $X_2$, $X_3$, $X_4$, $X_5$ and PUG each represents a divalent group and may be connected to each other to form a cyclic structure; and when n represents 2, two Z's, two $X_3$'s and two $X_4$'s may be the same or different. The compound used in the present invention is chemically stable and capable of releasing a photographically useful group at the desired rate, diffusibility of the photographically useful group released is large and the function area of the photographically useful group released can be effectively controlled. The silver halide color photographic light-sensitive material containing the compound has good stability during preservaton thereof and either provides a color image having good image qualities such as sharpness, graininess and color reproducibility, etc. or exhibits high sensitivity.

29 Claims, No Drawings

SILVER HALIDE COLOR PHOTOGRAPHIC LIGHT-SENSITIVE MATERIAL

FIELD OF THE INVENTION

The present invention relates to a silver halide color photographic light-sensitive material containing a novel compound which is capable of rendering a photographically useful group utilizable during development processing.

BACKGROUND OF THE INVENTION

It is known that upon color development of silver halide color photographic materials, the oxidation products of aromatic primary amine color developing agents react with couplers to form indophenol, indoaniline, indamine, azomethine, phenoxazine, phenazine and similar dyes, thereby forming color images. In this system, color reproduction is usually accomplished by the subtractive color process; silver halide emulsions selectively sensitive to blue, green and red, and yellow, magenta and cyan color image-forming agents in a complementary relation therewith are used. For example, acylacetanilide or dibenzoylmethane type couplers are used to form yellow color images; pyrazolone, pyrazolobenzimidazole, cyanoacetophenone or indazolone type couplers are mainly used to form magenta color images; and phenol type couplers, such as phenols and naphthols, are mainly used to form cyan color images.

It is also known that couplers are used not only to form dye images as described above but also for the purpose of releasing photographically useful groups. For example, U.S. Pat. Nos. 3,227,554 and 3,148,062, and *Journal of the American Chemical Society*, Vol. 72, page 1533 (1950) disclose couplers which release a development inhibitor or a dye from the coupling position thereof on reacting with the oxidation products of color developing agents.

Further, U.S. Pat. No. 3,705,801 discloses couplers which are capable of releasing a bleach inhibitor from the coupling position thereof after the reaction of the couplers with the oxidation products of the developing agents. More recently, Japanese Patent Application (OPI) No. 150845/82 discloses couplers which release a fogging agent from the coupling position thereof after the reaction of the couplers with the oxidation products of the developing agents.

Moreover, compounds which do not form dyes but release a photographically useful group upon the reaction with the oxidation products of the developing agents have also been known. For example, U.S. Pat. No. 3,930,863 discloses hydroquinones which release a development inhibitor.

As is well known from the above-described patent specifications, compounds releasing a photographically useful group are used for purposes such as improvement in color reproducibility, improvement in graininess, improvement in sharpness, or increase of sensitivity.

It is common knowledge in the photographic art that a technique to control the rate of releasing a photographically useful group and the rate of diffusion into an emulsion is more important than a technique to control the photographic function of the photographically useful group in the compounds capable of releasing a photographically useful group. It is also disclosed that as the diffusibility of the development inhibitors released increases, the sharpness is improved as described in U.S. Pat. No. 4,500,634. As an example of such techniques, couplers which release a photographically useful group having a timing group are proposed in U.S. Pat. Nos. 4,248,962 and 4,409,323, etc. These known couplers have good properties to some extent since the increase in the rate of coupling with these couplers is recognized in comparison with couplers wherein the photographically useful group is directly connected to the coupling position (for example, couplers as described in U.S. Pat. No. 3,227,554, etc.).

However, with these compounds the degree of diffusion of photographically useful groups into an emulsion is low and further improvement of the photographic properties has been desired. Furthermore, known couplers having a timing group have a problem in stability thereof during preservation of films containing them after coating, and they are disadvantageous in that their function is decreased or desensitization or formation of fog is accompanied by decomposition thereof.

SUMMARY OF THE INVENTION

Therefore, an object of the present invention is to provide a silver halide color photographic light-sensitive material which has good stability during preservation and either provides a color image having good image qualities such as sharpness, graininess and color reproducibility, etc. or has high sensitivity by using a novel compound which is chemically stable and capable of releasing a photographically useful group at the desired rate. Further diffusibility of the photographically useful group released is large and the function area of the photographically useful group released can be effectively controlled.

Other objects of the present invention will become apparent from the following detailed description and examples.

These objects of the present invention have been accomplished by a silver halide color photographic light-sensitive material comprising a support having thereon at least one silver halide emulsion layer, the color photographic light-sensitive material containing a compound capable of releasing a group represented by the general formula (I) described below upon the reaction with the oxidation product of a developing agent:

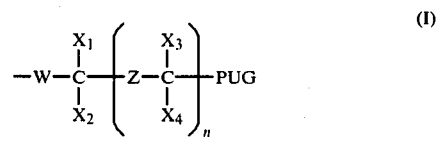

wherein W and Z each represents an oxygen atom, a sulfur atom or a group of

$X_1$, $X_2$, $X_3$, $X_4$ and $X_5$ each represents a hydrogen atom or an organic residue; PUG represents a photographically useful group; n represents 1 or 2; any two of $X_1$, $X_2$, $X_3$, $X_4$, $X_5$ and PUG each represents a divalent group and may be connected to each other to form a cyclic structure; and when n represents 2, two Z's, two $X_3$'s and two $X_4$'s may be the same or different.

DETAILED DESCRIPTION OF THE INVENTION

The compounds according to the present invention can eliminate the above-described defects and further have excellent photographic properties.

The compound according to the present invention releases a compound (a) described below upon the reaction with the oxidation product of a developing agent. The compound (a) diffuses in an emulsion and generates PUG through the reactions schematically illustrated as follows:

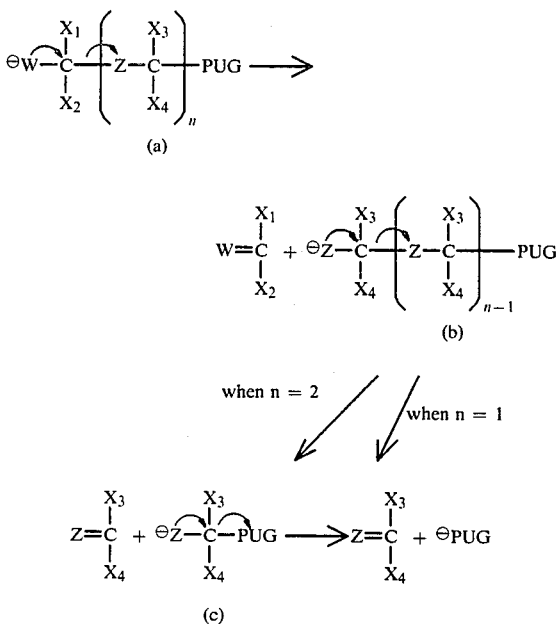

wherein, W, Z, $X_1$, $X_2$, $X_3$, $X_4$, PUG and n each has the same meaning as defined in the general formula (I).

As is apparent from the above described reaction scheme, the compound (a) which is released from the compound according to the present invention generates a photographically useful group (PUG) through a two-step reaction when n is 1 or a three-step reaction when n is 2.

The reaction rate of each step can be appropriately controlled by the selection of W, Z, $X_1$, $X_2$, $X_3$ and $X_4$. Further, the rate of diffusion of the compound (a), (b) or (c) in an emulsion can be appropriately controlled by the selection of W, Z, $X_1$, $X_2$, $X_3$ and $X_4$. Such control can be conducted by selecting the substituents which are electron donative or electron attractive or which are hydrophilic or hydrophobic.

The reason why the compuonds according to the present invention are excellent in their photographic properties will be explained below, but the explanation is not meant to be limiting.

It is generally known in reaction kinetics that an induction period is observed at the rate of forming the final product in a multi-step reaction. Such an induction period is not recognized in a one-step reaction, but it is remarkably observed as the number of steps of the reaction increases. The reason for the appearance of the induction period can be derived from the results of kinetic analysis. Since in the multi-step reaction, intermediates are present during the course of the reaction, the induction period naturally appears.

In the following, a one-step reaction and a two-step or three-step reaction are compared with each other assuming that the final products (PUG) are formed at a certain reaction time in a certain amount. That is, in the one-step reaction a large amount of PUG is formed at the beginning of the reaction and the amount gradually increases with the lapse of time. On the contrary, the amount of PUG formed is small at the beginning of the reaction and the amount thereof rapidly increases after the induction period in the two-step or three-step reaction. It is believed that these phenomena clearly explain why the compounds according to the present invention exhibit such excellent properties. More specifically, the compounds which are released from the compounds according to the present invention diffuse in an emulsion without immediately generating PUG and after the lapse of induction period they rapidly generate PUG. This means not only that the diffusibility of PUG is rendered large, but also that an area wherein PUG functions can be effectively controlled.

The compound which is capable of releasing the group represented by the general formula (I) upon the reaction with the oxidation product of a developing agent is a coupler or a hydroquinone. When the compound is a coupler, it is preferred that the group represented by the general formula (I) is connected to the coupling position thereof. However, the present invention includes any case wherein the group represented by the general formula (I) is released from a coupler as a result of the coupling reaction. For instance, in the case of connecting to the coupler sleleton, those as described in Japanese Patent Application (OPI) No. 209740/83 can be utilized. Further, cases wherein the group represented by the general formula (I) is not directly connected to the coupling position, but connected thereto through a timing group are also included in the present invention. Examples of the timing groups which can be employed in such cases are described in U.S. Pat. Nos. 4,248,962 and 4,409,323, British Pat. No. 2,096,783, Japanese Patent Application (OPI) Nos. 568371/82, 188035/82, 98728/83, 209737/83, 209738/83 and 209739/83, etc. Moreover, cases wherein the group represented by the general formula (I) is released from bis type couplers or polymer couplers are also included in the present invention.

Preferred compounds which can be used in the present invention can be represented by the following general formula (Ia):

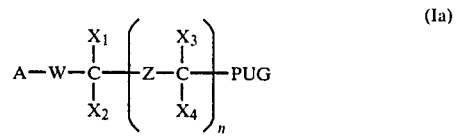

wherein W, Z, $X_1$, $X_2$, $X_3$, $X_4$, n and PUG each have the same meaning as defined in the general formula (I); and A represents a coupler residue or a hydroquinone residue.

In the general formula (Ia), A represents preferably a coupler residue.

Preferred examples of a yellow color image forming coupler residue represented by A include those of pivaloyl acetanilide type, benzoyl acetanilide type, malonic diester type, malondiamide type, dibenzoylmethane type, benzothiozolyl acetamide type, malonic ester monoamide type, benzothiazolyl acetate type, benzoxazolyl acetamide type, benzoxazolyl acetate type, benzimidazolyl acetamide type and benzimidazolyl acetate type; the coupler residues derived from hetero ring-substituted acetamides or hetero ring-substituted acetates involved in U.S. Pat. No. 3,841,880; the coupler residues derived from the acyl acetamides as described in U.S. Pat. No. 3,770,446, British Pat. No. 1,459,171, West German Patent Application (OLS) No. 2,503,099, Japanese Patent Application (OPI) No. 139738/75 and *Research Disclosure*, No. 15737; and the hetero ring type coupler residues as described in U.S. Pat. No. 4,046,574, etc.

Preferred examples of a magenta color image forming coupler residue represented by A include those of 5-oxo-2-pyrazoline type, pyrazolobenzimidazole type, pyrazolotriazole type, cyanoacetophenone type, pyrazoloimidazole type and N-hetero ring-substituted acylacetamide type coupler residues as described in West German Patent Application (OLS) No. 3,121,955, etc.

Preferred examples of a cyan color image forming coupler residue represented by A include those having a phenol nucleus or an α-naphthol nucleus.

Preferred examples of substantially non-color forming coupler residue represented by A include those of indanone type, acetophenone type, etc. and specific examples thereof are described in U.S. Pat. Nos. 4,052,213, 4,088,491, 3,632,345, 3,958,993, 3,961,959, 4,046,574 and 3,938,996, etc.

In the general formula (Ia), the group represented by PUG include, in detail, groups containing a development inhibitor, a development accelerator, a fogging agent, a dye, a developing agent, a coupler, a silver removing accelerator, a silver halide solvent, a competing compound and a silver removing inhibitor, etc.

An appropriate selection of PUG can be made depending on the purpose for which the compound is employed. That is, in order that a function of a certain photographically useful group is imagewise provided in a development step, the compounds represented by the general formula (Ia) which contain PUG having such a function in the structure thereof can be employed. Further, the photographic function can be exhibited at a desired rate depending on the purpose. Moreover, the photographic function of PUG can be controlled to a desired property depending on the purpose. This can be carried out by selecting the substituent on PUG, for example, whether the substituent is electron attractive or electron donative or whether it is hydrophilic or hydrophobic.

Preferred examples of PUG are set forth below.

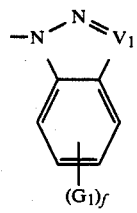 (P-1)

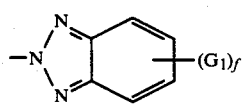 (P-2)

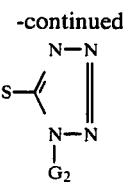 (P-3)

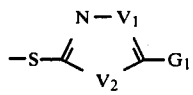 (P-4)

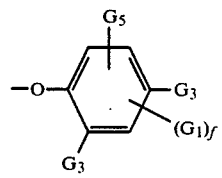 (P-5)

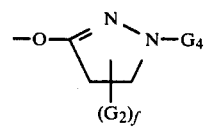 (P-6)

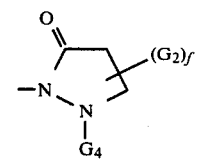 (P-7)

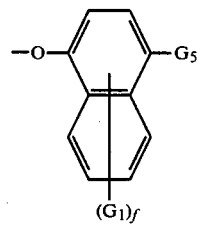 (P-8)

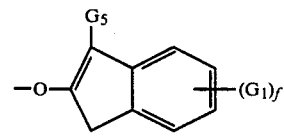 (P-9)

wherein $G_1$ represents a hydrogen atom, a halogen atom, an alkyl group (for example, a methyl group, an ethyl group, etc.), an acylamino group (for example, a benzamido group, a hexanamido group, etc.), an alkoxy group (for example, a butoxy group, a benzyloxy group, etc.), a sulfonamido group (for example, an octanesulfonamido group, a p-toluenesulfonamido group, etc.), an aryl group (for example, a phenyl group, a 4-chlorophenyl group, etc.), an alkylthio group (for example, a methylthio group, a butylthio group, etc.), an alkylamino group (for example, a cyclohexylamino group, etc.), an anilino group (for example, an anilino group, a 4-methoxycarbonylanilino group, etc.), an amino group, an alkoxycarbonyl group (for example, a methoxycarbonyl group, a butoxycarbonyl group, etc.), an acyloxy group (for example, an acetyl group, a butanoyl group, a benzoyl group, etc.), a nitro group, a cyano group, a sulfonyl group (for example, a butanesulfonyl group, a benzenesulfonyl group, etc.), an aryloxy group (for example, a phenoxy group, a naphthyloxy group, etc.), a hydroxy group, a thioamide group (for example, a butanethioamido group, a benzenethiocarbonamido group, etc.), a carbamoyl group (for example, a carbamoyl group, an N-arylcarbamoyl group, etc.), a sulfamoyl group (a sulfamoyl group, an N-arylsulfamoyl group, etc.), a carboxy group, a ureido group (for example, a ureido group, an N-ethylureido group, etc.) or an aryloxycarbonyl group (for example, a phenoxycarbonyl group, a 4-methoxyphenoxycarbonyl group, etc.), $G_2$ represents a hydrogen atom, an alkyl group (for example, a methyl group, an ethyl group, etc.) or an aryl group (for example, a phenyl group, a naphthyl group, etc.); $G_3$ represents a hydroxy group, a sulfonamido group (for example, a butanesulfonamido group, a benzenesulfonamido group, etc.), an amino group, an alkylamino group (for example, an ethylamino group, a cyclohexylamino group, etc.), an anilino group (for example, an anilino group, a 4-methylanilino group, etc.) or a hydrogen atom, two $G_3$'s in the general formula (P-5) may be the same or different provided that both $G_3$'s are not hydrogen atoms at the same time; $G_4$ represents an aryl group (for example, a phenyl group, a naphthyl group, etc.); $G_5$ represents a hydrogen atom, a heterocyclic thio group (for example, a group represented by the general formula (P-3) or (P-4), etc.) or a nitrogen-containing heterocyclic group condensed with a benzene ring (for example, a group represented by the general formula (P-1) or (P-2), etc.); f represents an integer of 1 to 2, when f is 2, $G_1$'s may be the same or different; $V_1$ represents a nitrogen atom or a group of

(wherein $G_1$ has the same meaning as defined above and may be the same or different from other $G_1$'s present in the molecule thereof); and $V_2$ represents an oxygen atom, a sulfur atom or a group of

(wherein $G_2$ has the same meaning as defined above), and in the general formula (P-4) when $V_1$ represents a group of

two $G_1$'s may be combined to form a condensed benzene ring (for example, a benzimidazolylthio group when $V_2$ represents —NH—, a benzoxazolylthio group when $V_2$ represents an oxygen atom, etc.).

When the groups represented by $G_1$, $G_2$, $G_3$, $G_4$ or $G_5$ in the general formula (P-1), (P-2), (P-3), (P-4), (P-5), (P-6), (P-7), (P-8) or (P-9) contain alkyl moieties, they may be any of substituted or unsubstituted, straight chain, branched chain or cyclic, saturated or unsaturated alkyl groups and contain from 1 to 22 carbon atoms, preferably from 1 to 10 carbon atoms. Further, when the groups represented by $G_1$, $G_2$, $G_3$, $G_4$ or $G_5$ contain aryl moieties, they may be substituted and contain from 6 to 10 carbon atoms, and are preferably substituted or unsubstituted phenyl groups.

The groups represented by the general formulae (P-1), (P-2), (P-3) and (P-4) are moieties of development inhibitors. The compounds represented by the general formula (Ia) wherein A represents a coupler residue and having one of these groups are generally called DIR couplers. In comparison with know DIR couplers however, the DIR coupling according to the present invention can effectively control the area in which development inhibitors function and further have sufficient stability. As a result, color photographic images having excellent properties with graininess, color reproducibility due to interimage effects and particularly sharpness can be obtained.

The groups represented by the general formulae (P-5), (P-6) and (P-7) are moieties of developing agents and have reducing function. Various effects of these groups on photographic properties are known. For example, when they reduce the oxidation products of developing agents, they are designated competing compounds and effective for improvement in graininess or sharpness, and when they reduce silver halides or when they are employed as auxiliary developing agents, sensitivity is increased.

The groups represented by the general formulae (P-8) and (P-9) are examples of coupler moieties. They function as competing couplers and are particularly preferred for improvement in graininess.

With the groups represented by the general formulae (P-5), (P-8) and (P-9) wherein $G_5$ represents a development inhibitor moiety such as a heterocyclic thio group, etc., the inhibiting action is further increased and thus the function as a DIR coupler can be effectively added.

In the general formulae (I) and (Ia), preferred examples of the organic residue represented by $X_1$, $X_2$, $X_3$ or $X_4$ include an alkyl group, an aryl group, an acyl group (for example, an acetyl group, a benzoyl group, etc.), a sulfonyl group (for example, a methanesulfonyl group, a benzenesulfonyl group, etc.), a carbamoyl group (for example, an ethylcarbamoyl group, a phenylcarbamoyl group, etc.), a sulfamoyl group (for example, an ethylsulfamoyl group, a phenylsulfamoyl group, etc.), an alkoxycarbonyl group (for example, an ethoxycarbonyl group, a butoxycarbonyl group, etc.), an aryloxycarbonyl group (for example, a phenoxycarbonyl group, a 4-methylphenoxycarbonyl group, etc.), an alkoxysulfonyl group (for example, a butoxysulfonyl group, an ethoxysulfonyl group, etc.), an aryloxysulfonyl group (for example, a phenoxysulfonyl group, a 4-methoxyphenoxysulfonyl group, etc.), a cyano group, a nitro group, a nitroso group, a carboxy group, a sulfo group, a thioacyl group (for example, a thioacetyl group, a thiobenzoyl group, etc.), a thiocarbamoyl group (for example, an ethylthiocarbamoyl group, etc.) and an imidazoyl group (for example, an N-ethylimidoyl group, etc.). When the above described substituents represented by $X_1$, $X_2$, $X_3$ or $X_4$ include alkyl moieties, they may be any of substituted or unsubstituted, saturated or unsaturated, straight chain, branched chain or cyclic groups and contain from 1 to 20, preferably from 1 to 10 carbon atoms. Further, when the above described substituents represented by $X_1$, $X_2$, $X_3$ or $X_4$ include aryl moieties, they may be substituted or unsubstituted phenyl groups or substituted or unsubstituted naphthyl groups and are preferably substituted or unsubstituted phenyl groups.

In the general formulae (I) and (Ia), when W or Z represents the group of

X₅ represents a hydrogen atom or any of the organic residues as described for X₁, X₂, X₃ or X₄ above.

Any two of X₁, X₂, X₃, X₄ and X₅ each represents a divalent group and may be connected each other to form a cyclic structure. Preferred examples of the cyclic structure are shown below.

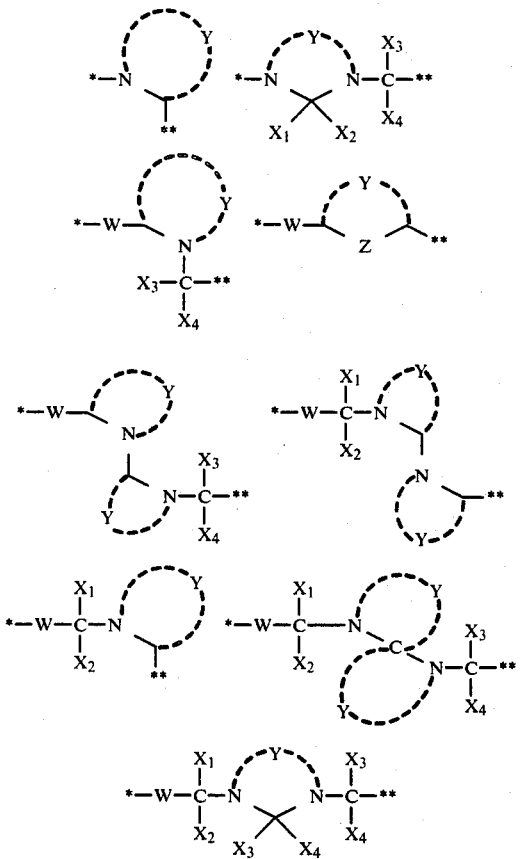

wherein a bond indicated by * denotes the position at which the group is connected to A; a bond indicated by ** denotes the position at which the group is connected to PUG; W, Z, X₁, X₂, X₃ and X₄ each has the same meaning as defined for the general formula (Ia); and Y represents a divalent organic residue necessary for forming a 4-membered, 5-membered or 6-membered ring.

PUG and any one of X₁, X₂, X₃ and X₅ each represents a divalent group and may be connected each other to form a cyclic structure. A preferred example of the cyclic structure is shown below.

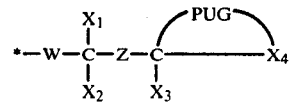

wherein a bond indicated by * denotes the position at which the group is connected to A; W, Z, X₁, X₂ and X₃ each has the same meaning as defined for the general formula (Ia); and X₄ and PUG each represents a divalent group and are connected each other to form a cyclic structure together with the carbon atom connected to X₄.

Preferred examples of the divalent organic residue represented by Y include the following groups:

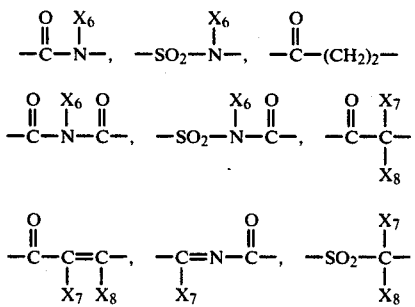

wherein X₆, X₇ and X₈ each represents a hydrogen atom or any of the organic residues as described for X₁, X₂, X₃, X₄ or X₅ above.

Further, the effects of the present invention are particularly exhibited when A in the general formula (Ia) represents a coupler residue represented by the general formula (II), (III), (IV), (V), (VI), (VII), (VIII), (IX), (X), (XI) or (XII) described below. These couplers are preferred because of their high coupling rates.

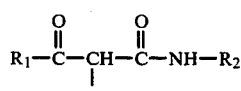  (II)

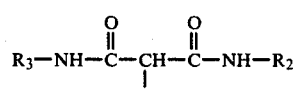  (III)

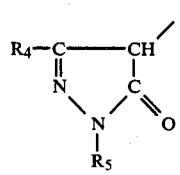  (IV)

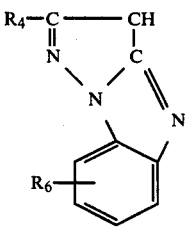  (V)

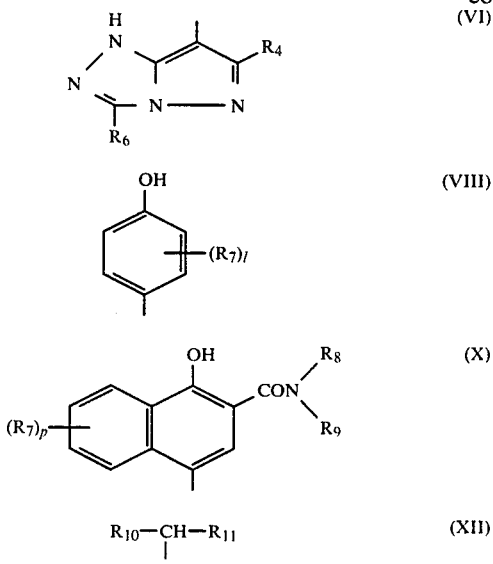
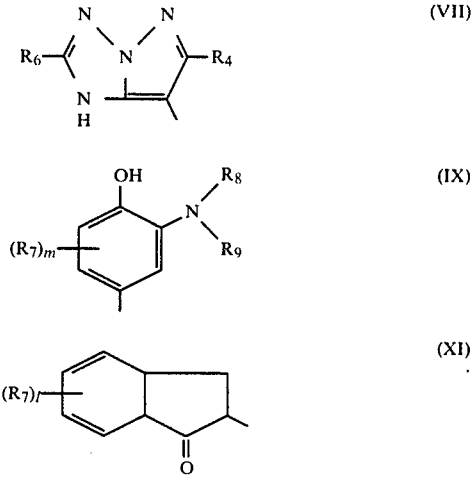

$$R_{10}-CH-R_{11} \quad \text{(XII)}$$

In the above-described formulae, a free bond attached to the coupling position indicates a position to which the group represented by the general formula (I) is connected. When $R_1$, $R_2$, $R_3$, $R_4$, $R_5$, $R_6$, $R_7$, $R_8$, $R_9$, $R_{10}$ or $R_{11}$ in the above-described formulae contains a diffusion-resistant group, it is selected so that the total number of carbon atoms included therein is from 8 to 32 and preferably from 10 to 22. On the other hand, when it does not contain a diffusion-resistant group, the total number of carbon atoms included therein is preferably not more than 15.

In the following, $R_1$ to $R_{11}$, l, m and p in the above-described general formulae (II) to (XII) are explained.

In the above-described formulae, $R_1$ represents an aliphatic group, an aromatic group, an alkoxy group or a heterocyclic group; and $R_2$ and $R_3$ each represents an aromatic group or a heterocyclic group.

The aliphatic groups represented by $R_1$ is preferably an aliphatic group containing from 1 to 22 carbon atoms, and may have substituents or not, and further, may have a chain form or a cyclic form. Preferable substituents therefor include an alkoxy group, an aryloxy group, an amino group, an acylamino group, a halogen atom, etc. which each may further have a substituent(s). Specific examples of aliphatic groups useful for $R_1$ include an isopropyl group, an isobutyl group, a tert-butyl group, an isoamyl group, a tert-amyl group, a 1,1-dimethylbutyl group, a 1,1-dimethylhexyl group, a 1,1-diethylhexyl group, a dodecyl group, a hexadecyl group, an octadecyl group, a cyclohexyl group, a 2-methoxyisopropyl group, a 2-phenoxyisopropyl group, a 2-p-tert-butylphenoxyisopropyl group, an α-aminoisopropyl group, an α-(diethylamino)isopropyl group, an α-(succinimido)isopropyl group, an α-(phthalimido)isopropyl group, an α-(benzenesulfonamido)isopropyl group, etc.

In the case that $R_1$, $R_2$ or $R_3$ represents an aromatic group (especially a phenyl group), it may have a substituent. Such an aryl group as a phenyl group, etc. may be substituted with an alkyl group, an alkenyl group, an alkoxy group, an alkoxycarbonyl group, an alkoxycarbonylamino group, an aliphatic amido group, an alkylsulfamoyl group, an alkylsulfonamido group, an alkylureido, alkyl-substituted succinimido group, etc.

each containing 32 or less carbon atoms. The alkyl group therein may include an alkyl group which contains an aromatic group such as phenylene in its main chain. Further, a phenyl group represented by $R_1$, $R_2$ or $R_3$ may be substituted with an aryloxy group, an aryloxycarbonyl group, an arylcarbamoyl group, an arylamido group, an arylsulfamoyl group, an arylsulfonamido group, an arylureido group etc., the aryl moiety of which groups each may be substituted with one or more alkyl groups wherein the number of carbon atoms is from 1 to 22 in total.

Furthermore, a phenyl group represented by $R_1$, $R_2$ or $R_3$ may be substituted with an amino group which includes an amino group substituted with a lower alkyl group having from 1 to 6 carbon atoms, a hydroxy group, a carboxy group, a sulfo group, a nitro group, a cyano group, a thiocyano group or a halogen atom.

In addition, $R_1$, $R_2$ or $R_3$ may represent a substituent formed by condensing a phenyl group and another ring, such as a naphthyl group, a quinolyl group, an isoquinolyl group, a chromanyl group, a coumaranyl group, a tetrahydronaphthyl group, etc. These substituents may further have substituents in themselves.

In the case that $R_1$ represents an alkoxy group, the alkyl moiety thereof represents a straight chain or branched chain alkyl group having from 1 to 32 carbon atoms, preferably from 1 to 22 carbon atoms, an alkenyl group, a cyclic alkyl group or a cyclic alkenyl group, which each may be substituted with a halogen atom, an aryl group, an alkoxy group, etc.

In the case that $R_1$, $R_2$ or $R_3$ represents a heterocyclic group, the heterocyclic group is connected to the carbon atom of the carbonyl group of the acyl moiety or the nitrogen atom of the amido moiety of an α-acylacetamide compound through one of the carbon atoms forming the ring. Examples of such heterocyclic rings include thiophene, furan, pyran, pyrrole, pyrazole, pyridine, pyrazine, pyrimidine, pyridazine, indolizine, imidazole, thiazole, oxazole, triazine, thiadiazine, oxazine, etc. These rings may further have substituents on the individual rings.

In the above-described formula, $R_5$ represents a straight chain or branched chain alkyl group having from 1 to 32 carbon atoms, preferably from 1 to 22 carbon atoms (e.g., a methyl group, an isopropyl group, a tert-butyl group, a hexyl group, a dodecyl group, etc.), an alkenyl group (e.g., an allyl group, etc.), a cyclic alkyl group (e.g., a cyclopentyl group, a cyclohexyl group, a norbornyl group, etc.), an aralkyl group (e.g., a benzyl group, a β-phenylethyl group, etc.), a cyclic alkenyl group (e.g., a cyclopentenyl group, a cyclohexenyl group, etc.), etc., which groups each may be substituted with a halogen atom, a nitro group, a cyano group, an aryl group, an alkoxy group, an aryloxy group, a carboxy group, an alkylthiocarbonyl group, an arylthiocarbonyl group, an alkoxycarbonyl group, an aryloxycarbonyl group, a sulfo group, a sulfamoyl group, a carbamoyl group, an acylamino group, a diacylamino group, a ureido group, a urethane group, a thiourethane group, a sulfonamido group, a heterocyclic group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxy group, a mercapto group, etc.

$R_5$ may further represent an aryl group (e.g., a phenyl group, an α- or β-naphthyl group, etc.). The aryl group may have one or more substituents. Specific examples of the substituents include an alkyl group, an alkenyl group, a cyclic alkyl group, an aralkyl group, a cyclic alkenyl group, a halogen atom, a nitro group, a cyano group, an aryl group, an alkoxy group, an aryloxy group, a carboxy group, an alkoxycarbonyl group, an aryloxycarbonyl group, a sulfo group, a sulfamoyl group, a carbamoyl group, an acylamino group, a diacylamino group, a ureido group, a urethane group, a sulfonamido group, a heterocyclic group, an arylsulfonyl group, an alkylsulfonyl group, an arylthio group, an alkylthio group, an alkylamino group, a dialkylamino group, an anilino group, an N-alkylanilino group, an N-arylanilino group, an N-acylanilino group, a hydroxy group, a mercapto group, etc. A more preferable group for $R_5$ is a phenyl group which is substituted with an alkyl group, an alkoxy group, a halogen atom, etc. at least at one of the o-positions, because it is effective to restrain coloration of couplers remaining in film layers due to light or heat.

Furthermore, $R_5$ may represent a heterocyclic group (e.g., a 5-membered or 6-membered heterocyclic ring containing as a hetero atom, a nitrogen atom, an oxygen atom or a sulfur atom, or a condensed ring thereof, with specific examples including a pyridyl group, a quinolyl group, a furyl group, a benzothiazolyl group, an oxazolyl group, an imidazolyl group, a naphthoxazolyl group, etc.), a heterocyclic group substituted with one or more substituents as defined for the above-described aryl group, an aliphatic acyl group, an aromatic acyl group, an alkylsulfonyl group, an arylsulfonyl group, an alkylcarbamoyl group, an arylcarbamoyl group, an alkylthiocarbamoyl group or an arylthiocarbamoyl group.

In the above-described general formulae, $R_4$ represents a hydrogen atom, a straight chain or branched chain alkyl group having from 1 to 32 carbon atoms, preferably from 1 to 22 carbon atoms, an alkenyl group, a cyclic alkyl group, an aralkyl group or a cyclic alkenyl group (which each may have one or more substituents as defined for the above-described substituent $R_5$), an aryl group or a heterocyclic group (which each also may have one or more substituents as defined for the above-described substituent $R_5$), an alkoxycarbonyl group (e.g., a methoxycarbonyl group, an ethoxycarbonyl group, a stearyloxycarbonyl group, etc.), an aryloxycarbonyl group (e.g., a phenoxycarbonyl group, a naphthoxycarbonyl group, etc.), an aralkyloxycarbonyl group (e.g., a benzyloxycarbonyl group, etc.), an alkoxy group (e.g., a methoxy group, an ethoxy group, a heptadecyloxy group, etc.), an aryloxy group (e.g., a phenoxy group, a tolyloxy group, etc.), an alkylthio group (e.g., an ethylthio group, a dodecylthio group, etc.), an arylthio group (e.g., a phenylthio group, an α-naphthylthio group, etc.), a carboxy group, an acylamino group (e.g., an acetylamino group, a 3-[(2,4-di-tert-amylphenoxy)acetamido]benzamido group, etc.), a diacylamino group, an N-alkylacylamino group (e.g., an N-methylpropionamido group, etc.), an N-arylacylamino group (e.g., an N-phenylacetamido group, etc.), a ureido group (e.g., a ureido group, an N-arylureido group, an N-alkylureido group, etc.), a urethane group, a thiourethane group, an arylamino group (e.g., a phenylamino group, an N-methylanilino group, a diphenylamino group, an N-acetylanilino group, a 2-chloro-5-tetradecanamidoanilino group, etc.), an alkylamino group (e.g., a n-butylamino group, a methylamino group, a cyclohexylamino group, etc.), a cycloamino group (e.g., a piperidino group, a pyrrolidino group, etc.), a heterocyclic amino group (e.g., a 4-pyridylamino group, a 2-benzoxazolylamino group, etc.), an alkylcarbonyl group (e.g., a methylcarbonyl group, etc.), an arylcarbonyl group (e.g., a phenylcarbonyl group, etc.), a sulfonamido group (e.g., an alkylsulfonamido group, an arylsulfonamido group, etc.), a carbamoyl group (e.g., an ethylcarbamoyl group, a dimethylcarbamoyl group, an N-methylphenylcarbamoyl group, an N-phenylcarbamoyl group, etc.), a sulfamoyl group (e.g., an N-alkylsulfamoyl group, an N,N-dialkylsulfamoyl group, an N-arylsulfamoyl group, an N-alkyl-N-arylsulfamoyl group, an N,N-diarylsulfamoyl group, etc.), a cyano, a hydroxy group, a mercapto group, a halogen atom or a sulfo group.

In the above-described formulae, $R_6$ represents a hydrogen atom, or a straight chain or branched chain alkyl group having from 1 to 32 carbon atoms, preferably from 1 to 22 carbon atoms, an alkenyl group, a cyclic alkyl group, an aralkyl group or a cyclic alkenyl group, which each may have one or more substituents as defined for the above-described substituent $R_5$.

Further, $R_6$ may represent an aryl group or a heterocyclic group, which each may have one or more substituents as defined for the above-described substituent $R_5$.

Furthermore, $R_6$ may represent a cyano group, an alkoxy group, an aryloxy group, a halogen atom, a carboxy group, an alkoxycarbonyl group, an aryloxycarbonyl group, an acyloxy group, a sulfo group, a sulfamoyl group, a carbamoyl group, an acylamino group, a diacylamino group, a ureido group, a urethane group, a sulfonamido group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxy group or a mercapto group.

In the above-described formulae, $R_7$, $R_8$ and $R_9$ each represents a group which has been employed in conventional 4-equivalent type phenol or α-naphthol couplers. Specifically, $R_7$ represents a hydrogen atom, a halogen atom, an alkoxycarbonylamino group, an aliphatic hydrocarbon residue, an N-arylureido group, an acylamino group, an $—O—R_{12}$ group or an $—S—R_{12}$ group (wherein $R_{12}$ is an aliphatic hydrocarbon residue). When two or more of $R_7$'s are present in one molecule, they may be different from each other. The above-described aliphatic hydrocarbon residues include those having substituents. In the case that these substituents include an aryl group, the aryl group may have one or more substituents as defined for the above-described substituent $R_5$.

$R_8$ and $R_9$ each represents an aliphatic hydrocarbon residue, an aryl group or a heterocyclic group. One of them may be a hydrogen atom. The above-described groups for $R_8$ and $R_9$ may further have certain substituents. Furthermore, $R_8$ and $R_9$ may combine with each other and form a nitrogen-containing heterocyclic nucleus. More specifically, the above-described aliphatic hydrocarbon residue includes both saturated and unsaturated residues, wherein each may have a straight chain form, a branched chain form or a cyclic form. Preferred examples thereof include an alkyl group (e.g., a methyl group, an ethyl group, a propyl group, an isopropyl group, a butyl group, a tert-butyl group, an isobutyl group, a dodecyl group, an octadecyl group, a cyclobutyl group, a cyclohexyl group, etc.) and an alkenyl group (e.g., an allyl group, an octenyl group, etc.). The above-described aryl group includes a phenyl group, a naphthyl group, etc. Representatives of the above-described heterocyclic groups include a pyridinyl group, a quinolyl group, a thienyl group, a piperidyl group, an imidazolyl group, etc. These aliphatic hydrocarbon residues, aryl groups and heterocyclic groups each may be substituted with a halogen atom, a nitro group, a hydroxy group, a carboxy group, an amino group, a substituted amino group, a sulfo group, an alkyl group, an alkenyl group, an aryl group, a heterocyclic group, an alkoxy group, an aryloxy group, an arylthio group, an arylazo group, an acylamino group, a carbamoyl group, an ester group, an acyl group, an acyloxy group, a sulfonamido group, a sulfamoyl group, a sulfonyl group, a morpholino group, etc.

In the above-described formulae, l represents an integer of 1 to 4, m represents an integer of 1 to 3, and p represents an integer of 1 to 5.

In the above-described formula, $R_{10}$ represents an arylcarbonyl group, an alkanoyl group having from 2 to 32 carbon atoms, preferably from 2 to 22 carbon atoms, an arylcarbamoyl group, an alkanecarbamoyl group having from 2 to 32 carbon atoms, preferably from 2 to 22 carbon atoms, an alkoxycarbonyl group having from 1 to 32 carbon atoms, preferably from 1 to 22 carbon atoms or an aryloxycarbonyl group, which each may be substituted. Examples of the substituents include an alkoxy group, an alkoxycarbonyl group, an acylamino group, an alkylsulfamoyl group, an alkylsulfonamido group, an alkylsuccinimido group, a halogen atom, a nitro group, a carboxy group, a nitrile group, an alkyl group, an aryl group, etc.

In the above-described formula, $R_{11}$ represents an arylcarbonyl group, an alkanoyl group having from 2 to 32 carbon atoms, preferably from 2 to 22 carbon atoms, an arylcarbamoyl group, an alkanecarbamoyl group having from 2 to 32 carbon atoms, preferably from 2 to 22 carbon atoms, an alkoxycarbonyl group having from 1 to 32 carbon atoms, preferably from 1 to 22 carbon atoms, an aryloxycarbonyl group, an alkanesulfonyl group having from 1 to 32 carbon atoms, preferably from 1 to 22 carbon atoms, an arylsulfonyl group, an aryl group or a 5-membered or 6-membered heterocyclic group (containing as a hetero atom, a nitrogen atom, an oxygen atom or a sulfur atom, with specific examples including a triazolyl group, an imidazolyl group, a phthalimido group, a succinimido group, a furyl group, a pyridyl group, a benzotriazolyl group, etc.), which each may have one or more substituents as defined for the above-described substituent $R_{10}$.

The compounds according to the present invention are preferably employed together with other conventional couplers. They can be used in a range from 0.1 mol% to 30 mol%, preferably from 1 mol% to 20 mol% based on main couplers used.

The compounds according to the present invention can be employed in any of a high sensitive layer, a low sensitive layer and an intermediate layer, etc. depending on the purposes.

Specific examples of the compounds used in the present invention are set forth below, but the present invention should not be construed as being limited thereto.

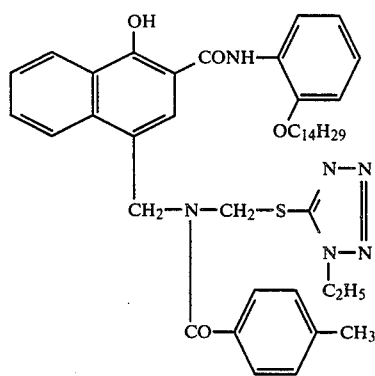

(1)

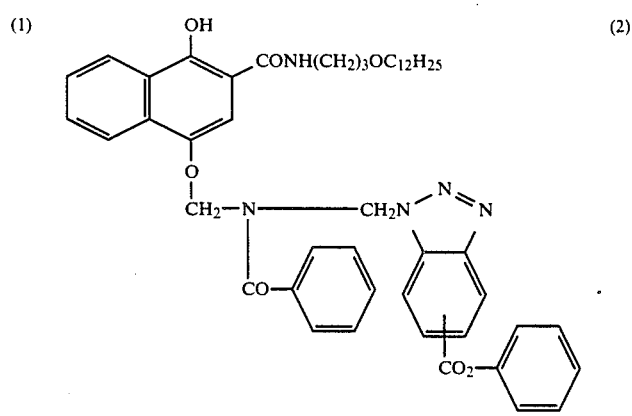

(2)

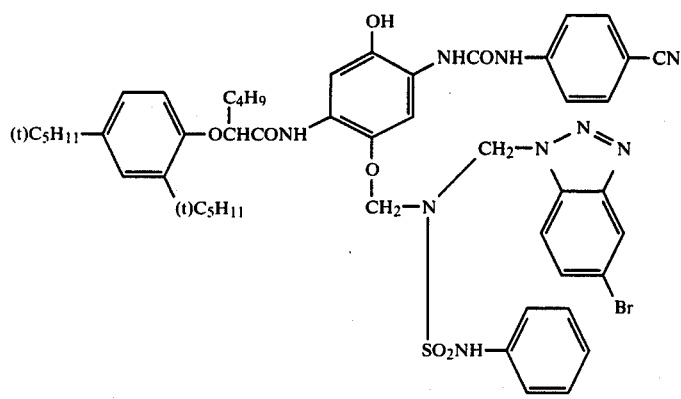
(3)
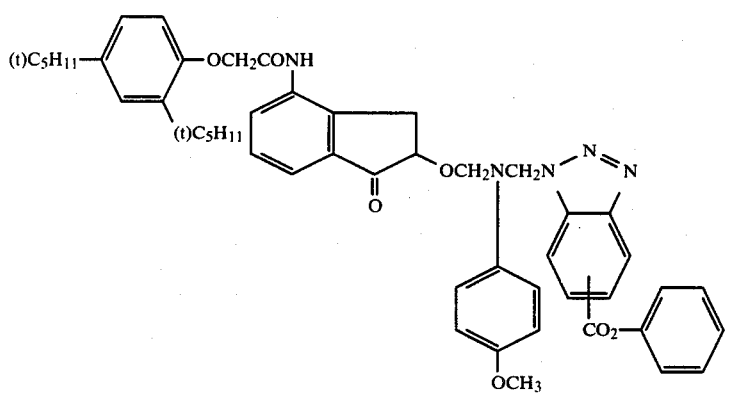
(4)
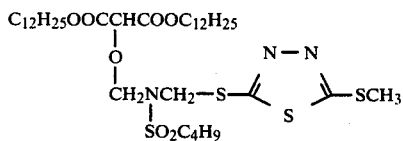
(5)
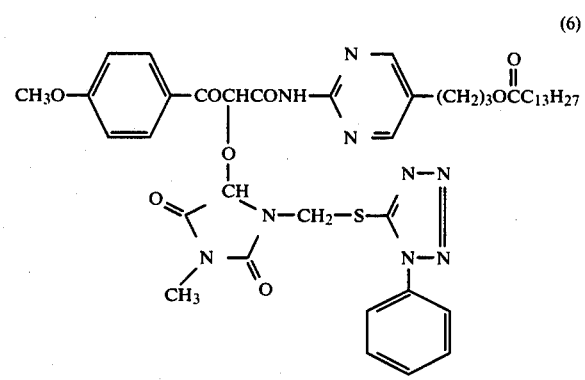
(6)
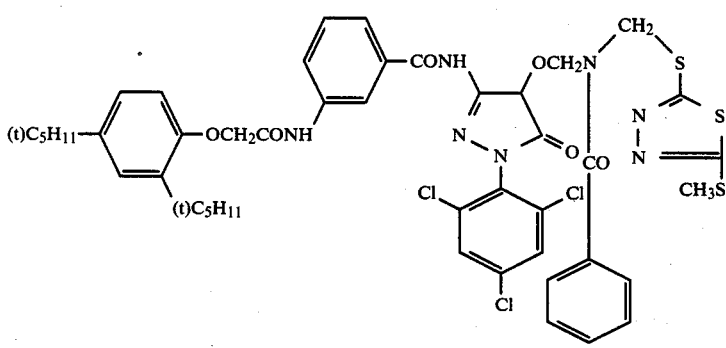
(7)

-continued
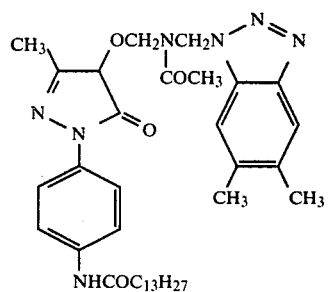
(8)
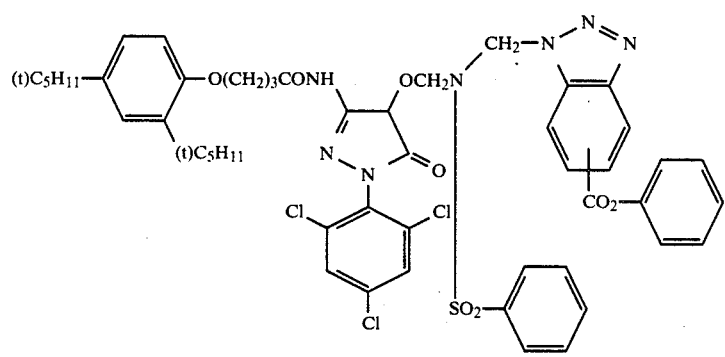
(9)
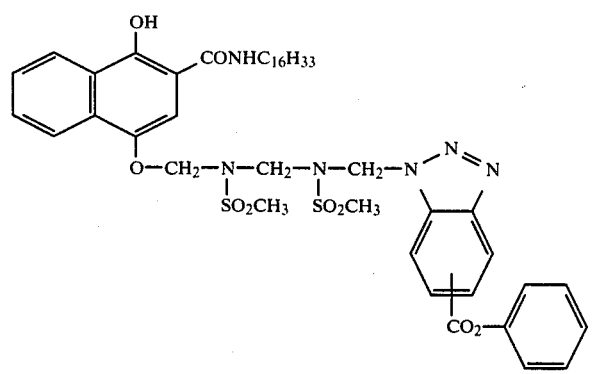
(10)
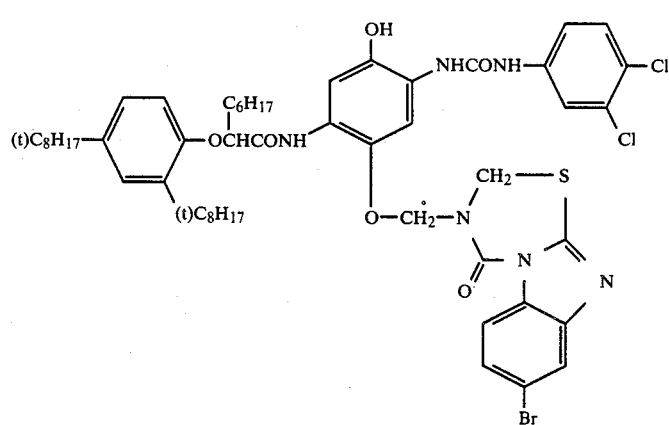
(11)

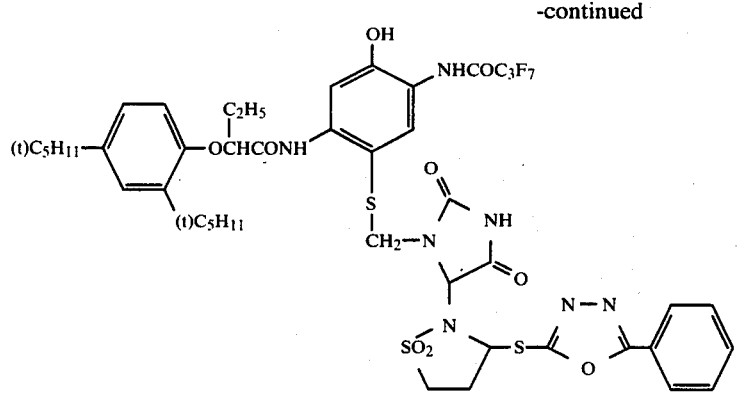
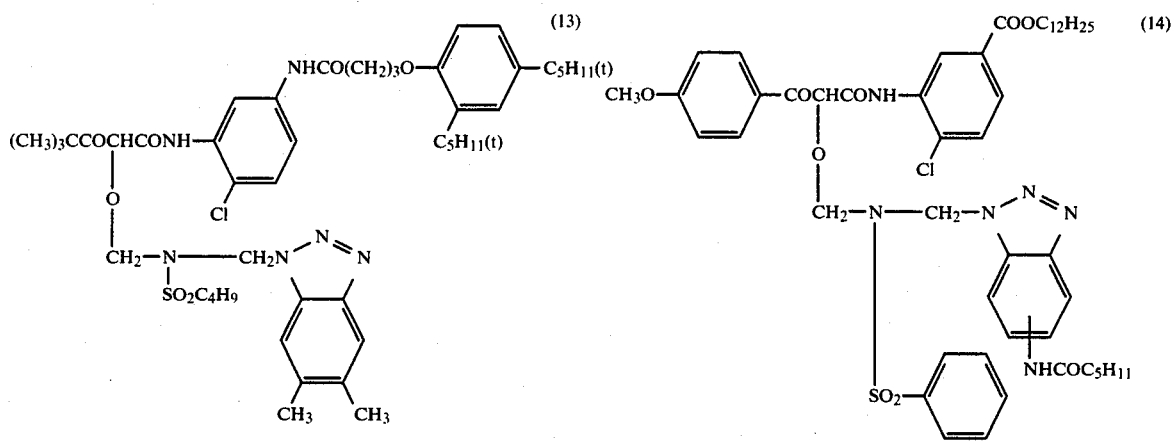
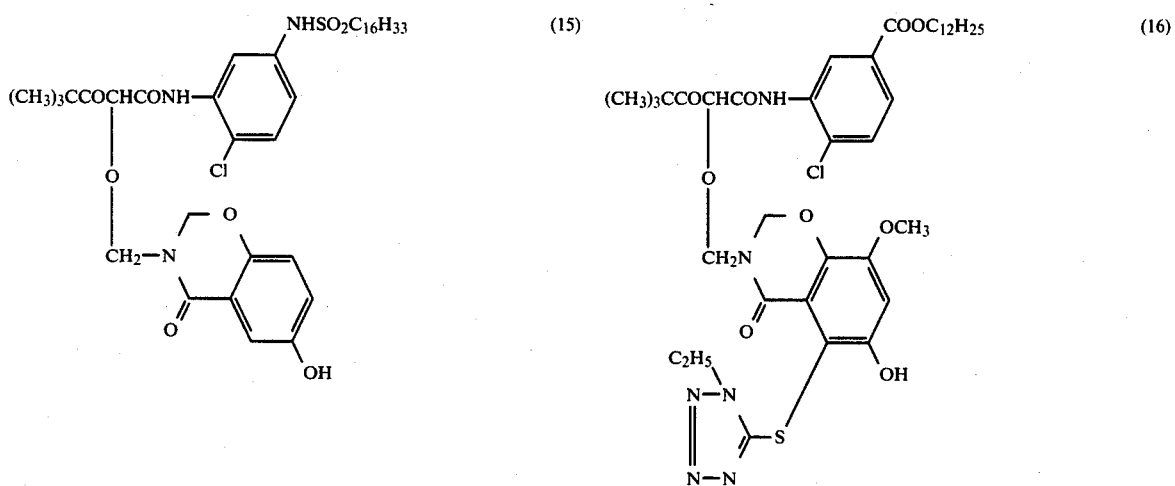
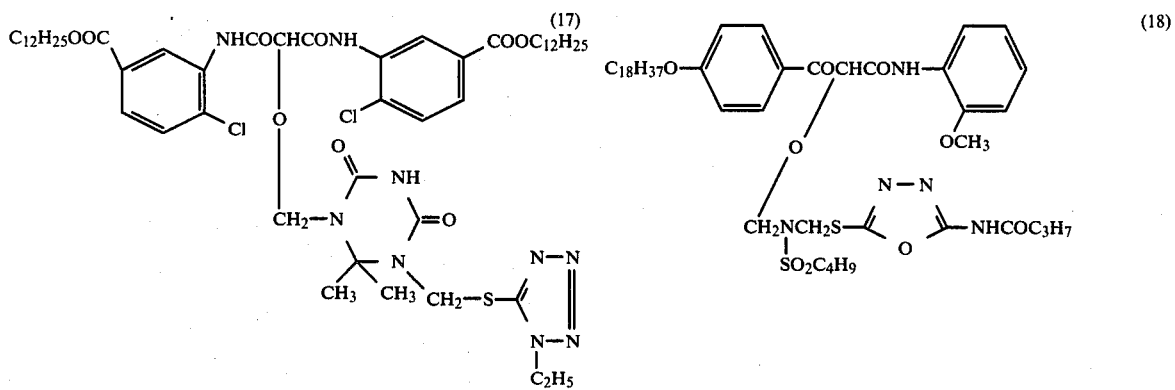

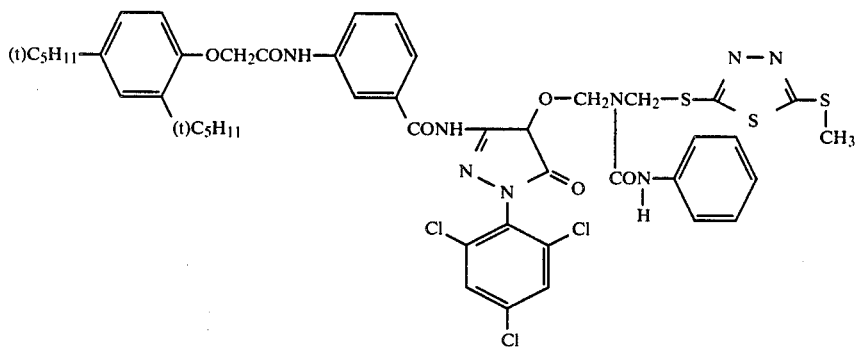
(19)
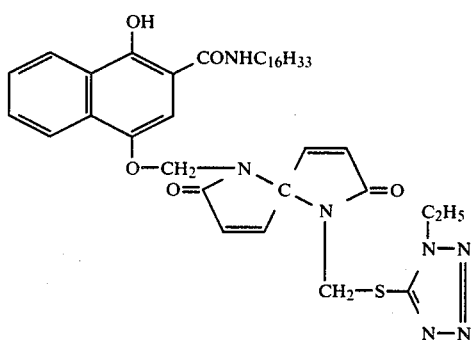
(20)
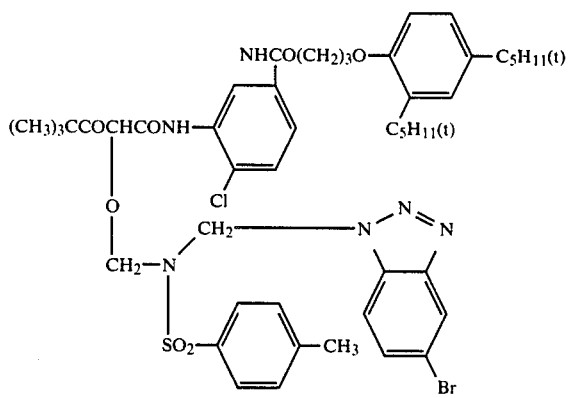
(21)
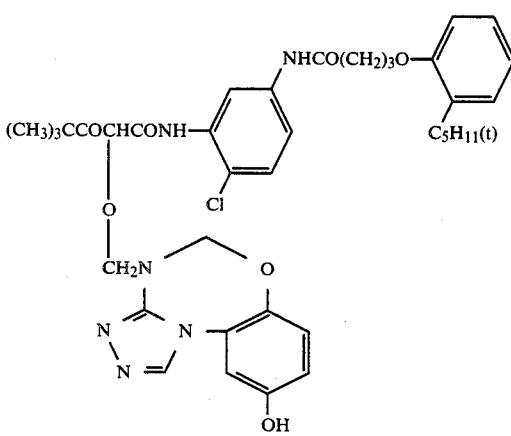
(22)
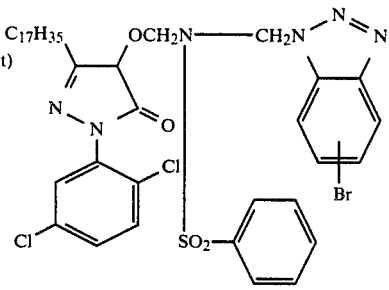
(23)
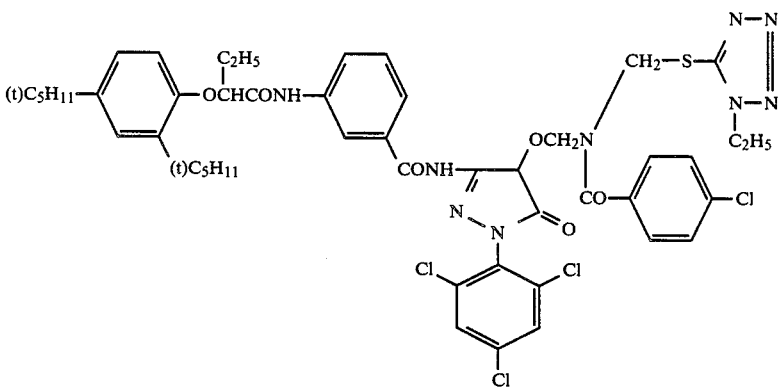
(24)

-continued
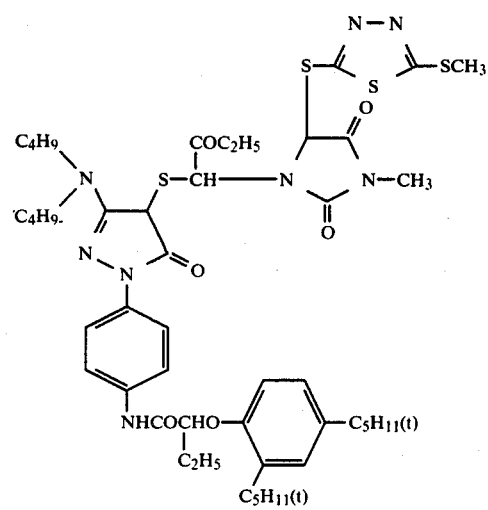 (25)
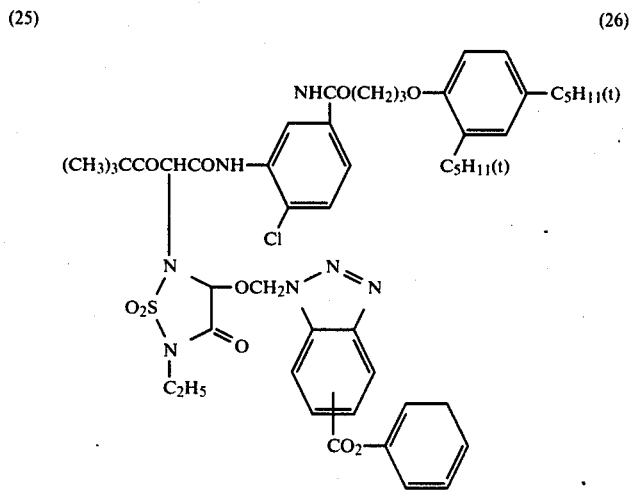 (26)
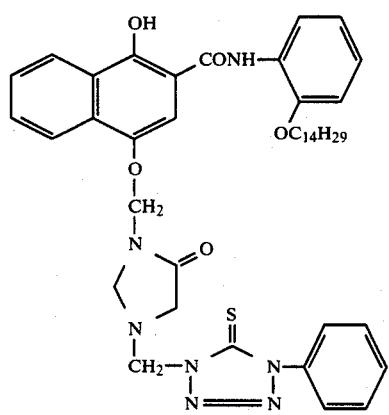 (27)
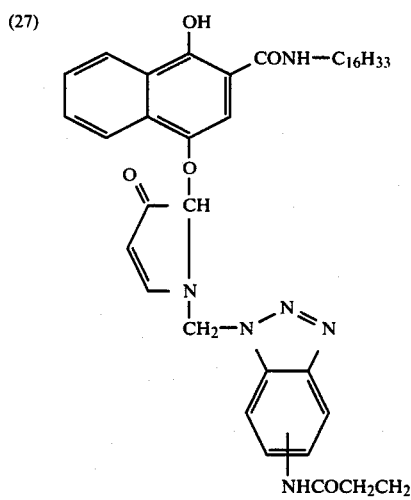 (28)
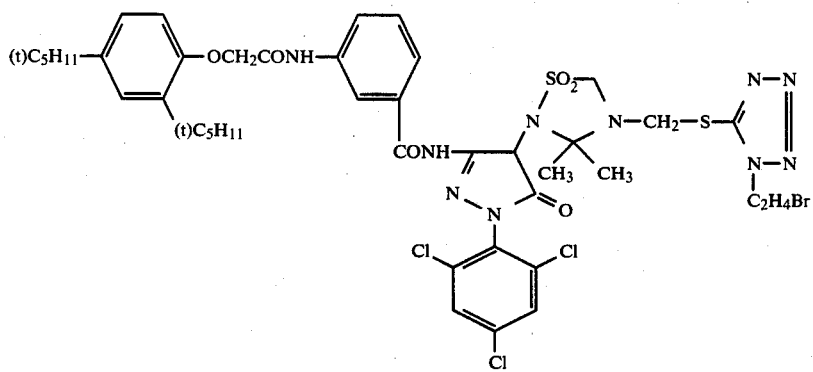 (29)

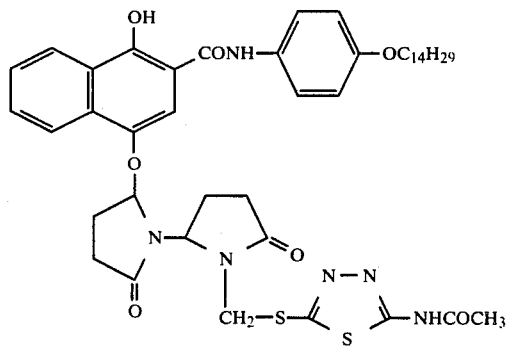

The compounds according to the present invention can be generally synthesized according to the following synthesis route;

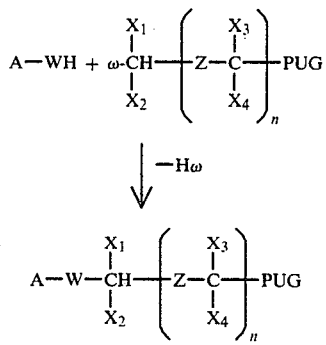

wherein w represents a chlorine atom or a bromine atom; and A, W, Z, $X_1$, $X_2$, $X_3$, $X_4$, PUG and n each has the same meaning as defined above.

The reaction described above is ordinarily carried out using a base. Examples of the base include potassium hydroxide, sodium hydroxide, potassium tert-butoxide, sodium methoxide, triethylamine and sodium hydride, etc. As a reaction solvent, a polar solvent (for example, N,N-dimethylformamide, dimethylsulfoxide, ethanol, etc.) or a non-polar solvent (for example, toluene, ethyl acetate, etc.) can be employed.

Typical examples of syntheses of the compounds according to the present invention are specifically shown below.

SYNTHESIS EXAMPLE 1

Synthesis of Compound (1)

Compound (1) was synthesized according to the following synthesis route:

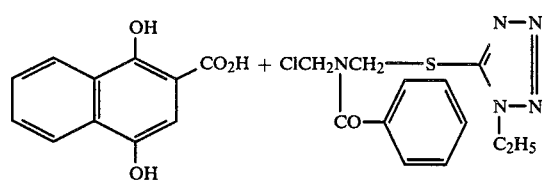

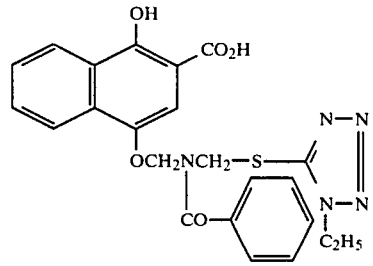

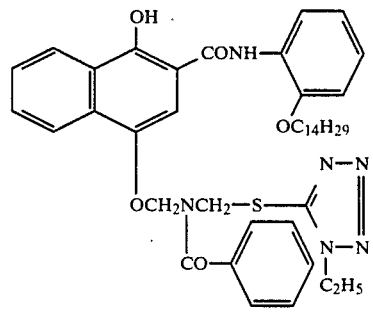

Compound (1)

Step (1): Synthesis of Compound 3

24.6 g of Compound 1 was mixed with 100 ml of N,N-dimethylformamide and 47 g of a 28% methanol solution of sodium methoxide was added dropwise thereto at room temperature (25° C. or below). To the solution was added dropwise 200 ml of an N,N-dimethylformamide solution containing 37.3 g of Compound 2 dissolved at room temperature. After being subjected to reaction for 20 minutes at 25° C. or below, the reaction mixture was neutralized with aqueous hydrochloric acid and extracted with 500 ml of ethyl acetate. After washing with water, the oil layer was collected and dried with sodium sulfate. The solvent was distilled off until a half of the original volume under a reduced pressure and the crystals thus-precipitated were collected by filtration to obtain 33 g of Compound 3.

Compound 2 used in the above synthesis can be synthesized according to the following synthesis route by ordinary manners.

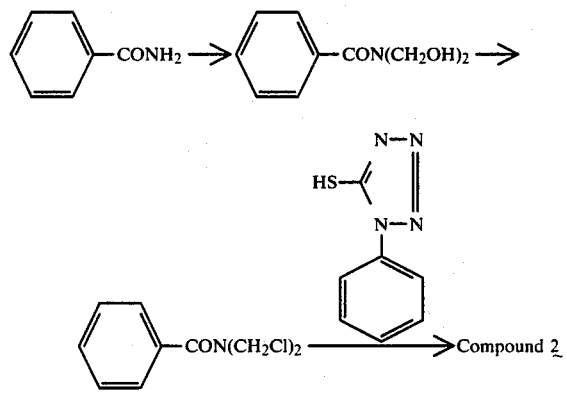

Step (2): Synthesis of Compound (1)

30 g of Compound 3 obtained in step (1) above and 19.2 g of 2-tetradecyloxyaniline (Compound 4) were mixed with 200 ml of N,N-dimethylformamide and to the solution was added dropwise 100 ml of N,N-dimethylformamide solution containing 12.9 g of N,N'-dicyclohexylcarbodiimide dissolved at 5° C. The temperature was gradually raised to room temperature and the mixture was subjected to reaction for 3 hours. The crystals (N,N-dicyclohexylurea) thus-precipitated were removed by filtration, to the filtrate was added 500 ml of ethyl acetate and the mixture was placed in a separatory funnel and washed with water. The oil layer was dried with sodium sulfate and the solvent was distilled off under a reduced pressure. The residue was recrystallized from a solvent mixture of ethyl acetate and hexane to obtain 23.6 g of the desired Compound (1).

SYNTHESIS EXAMPLE 2

Synthesis of Compound (7)

Compound (7) was synthesized according to the following synthesis route:

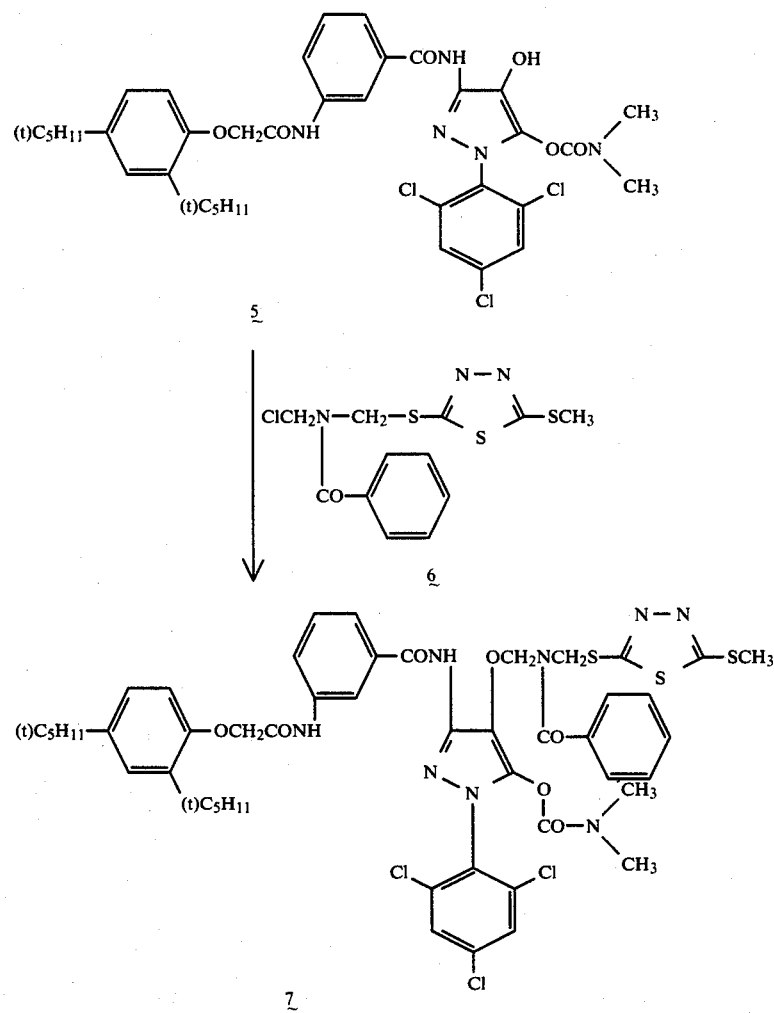

-continued

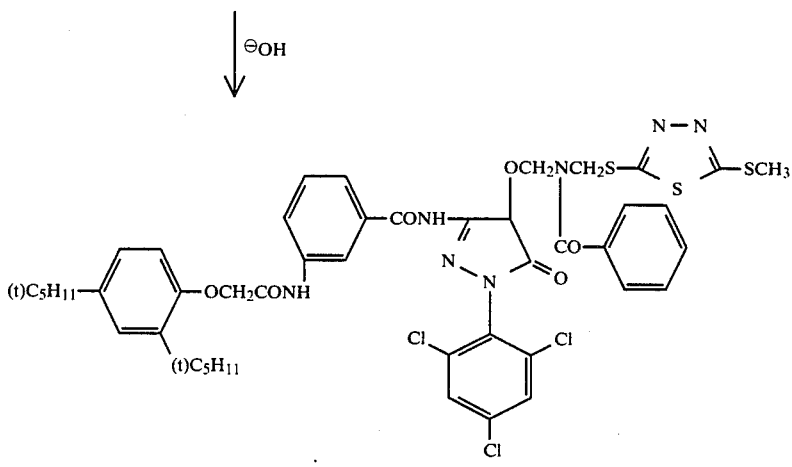

Compound (7)

38.0 g of Compound 5 (which was synthesized by the method as described in Japanese Patent Application (OPI) No. 70871/82) and 22.5 g of Compound 6 were dissolved in 200 ml of N,N-dimethylformamide and to the solution was added 11.2 g of potassium tert-butoxide divided into three parts at room temperature (25° C.) over a period of 30 minutes. The mixture was stirred at room temperature for one day, 50 ml of water was added thereto and the mixture was heated at 50° C. and stirred for 30 minutes. After cooling to room temperature, 800 ml of ethyl acetate was added thereto and the mixture was placed in a separatory funnel and washed with water, then with 1N diluted hydrochloric acid and thereafter further with water until the washed water became neutral. The oil layer was dried with sodium sulfate and the solvent was distilled off under a reduced pressure. The residue was crystallized using acetonitrile to obtain 19.3 g of the desired Compound (7).

Compound 6 used in the above synthesis can be synthesized in a similar manner to that for the synthesis of Compound 4 as described above.

In order to incorporate the compounds according to the present invention and couplers to be used together therewith into a silver halide emulsion layer in the present invention, known methods, including those described, e.g., in U.S. Pat. No. 2,322,027 can be used. For example, they can be dissolved in a solvent and then dispersed in a hydrophilic colloid. Examples of solvents usable for this process include organic solvents having a high boiling point, such as alkyl esters of phthalic acid (e.g., dibutyl phthalate, dioctyl phthalate, etc.), phosphoric acid esters (e.g., diphenyl phosphate, triphenyl phosphate, tricresyl phosphate, dioctyl butyl phosphate, etc.), citric acid esters (e.g., tributyl acetyl citrate, etc.), benzoic acid esters (e.g., octyl benzoate, etc.), alkylamides (e.g., diethyl laurylamides, etc.), esters of fatty acids (e.g., dibutoxyethyl succinate, diethyl azelate, etc.), trimesic acid esters (e.g., tributyl trimesate, etc.), or the like; and organic solvents having a boiling point of from about 30° to about 150° C., such as lower alkyl acetates (e.g., ethyl acetate, butyl acetate, etc), ethyl propionate, secondary butyl alcohol, methyl isobutyl ketone, β-ethoxyethyl acetate, methyl cellosolve acetate, or the like. Mixtures of the organic solvents having a high boiling point and the organic solvents having a low boiling point described above can also be used.

It is also possible to utilize the dispersing method using polymers, as described in Japanese Patent Publication No. 39853/76 and Japanese Patent Application (OPI) No. 59943/76.

Of the couplers, those having an acid group, such as a carboxylic acid group or a sulfonic acid group, can be introduced into hydrophilic colloids as an aqueous alkaline solution.

As the binder or the protective colloid for the photographic emulsion layers or intermediate layers of the photographic light-sensitive material of the present invention, gelatin is advantageously used, but other hydrophilic colloids can be used alone or together with gelatin.

As gelatin in the present invention, not only lime-processed gelatin, but also acid-processed gelatin may be employed. The methods for preparation of gelatin are described in greater detail in Ather Veis, *The Macromolecular Chemistry of Gelatin*, Academic Press (1964).

As the above-described hydrophilic colloids other than gelatin, it is possible to use proteins such as gelatin derivatives, graft polymers of gelatin and other polymers, albumin, casein, etc.; saccharides such as cellulose derivatives such as hydroxyethyl cellulose, carboxymethyl cellulose, cellulose sulfate, etc., sodium alginate, starch derivatives, etc.; and various synthetic hydrophilic high molecular weight substances such as homopolymers or copolymers, for example, polyvinyl alcohol, polyvinyl alcohol semiacetal, poly-N-vinylpyrrolidone, polyacrylic acid, polymethacrylic acid, polyacrylamide, polyvinyl imidazole, polyvinyl pyrazole, etc.

In the photographic emulsion layer of the photographic light-sensitive meterial used in the present invention, any of silver bromide, silver iodobromide, silver iodochlorobromide, silver chlorobromide and silver chloride may be used as the silver halide. A preferred silver halide is silver iodobromide containing 15 mol% or less of silver iodide. A silver iodobromide emulsion containing from 2 mol% to 12 mol% of silver iodide is particularly preferred.

Although the mean grain size of silver halide particles in the photographic emulsion (the mean grain size being determined with a grain diameter in those particles which are spherical or nearly spherical, and an edge length in those particles which are cubic as a grain size, and is expressed as a mean value calculated from projected areas) is not particularly limited, it is preferably $3\mu$ or less.

The distribution of grain size may be broad or narrow.

Silver halide particles in the photographic emulsion may have a regular crystal structure, e.g., a cubic or octahedral structure, an irregular crystal structure, e.g., a spherical or plate-like structure, or a composite structure thereof. In addition, silver halide particles composed of those having different crystal structures may be used.

Further, the photographic emulsion wherein at least 50 percent of the total projected area of silver halide particles is super tabular silver halide particles having a diameter at least five times their thickness may be employed.

The inner portion and the surface layer of silver halide particles may be different in phase. Silver halide particles may be those in which a latent image is formed mainly on the surface thereof, or those in which a latent image is formed mainly in the interior thereof.

The photographic emulsion used in the present invention can be prepared in any suitable manner, e.g., by the methods as described in P. Glafkides, *Chimie et Physique Photographique*, Paul Montel (1967), G. F. Duffin, *Photographic Emulsion Chemistry*, The Focal Press (1966), and V. L. Zelikman et al., *Making and Coating Photographic Emulsion*, The Focal Press (1964). That is, any of an acid process, a neutral process, an ammonia process, etc., can be employed.

Soluble silver salts and soluble halogen salts can be reacted by techniques such as a single jet process, a double jet process, and a combination thereof. In addition, there can be employed a method (so-called reversal mixing process) in which silver halide particles are formed in the presence of an excess of silver ions.

As one system of the double jet process, a so-called controlled double jet process in which the pAg in a liquid phase where silver halide is formed is maintained at a predetermined level can be employed. This process can produce a silver halide emulsion in which the crystal form is regular and the grain size is nearly uniform.

Two or more kinds of silver halide emulsions which are prepared separately may be used as a mixture.

The formation or physical ripening of silver halide particles may be carried out in the presence of cadmium salts, zinc salts, lead salts, thallium salts, iridium salts or its complex salts, rhodium salts or its complex salts, iron salts or its complex salts, and the like.

For removal of soluble salts from the emulsion after precipitate formation or physical ripening, a well known noodle washing process in which gelatin is gelated may be used. In addition, a flocculation process utilizing inorganic salts having a polyvalent anion (e.g., sodium sulfate), anionic surface active agents, anionic polymers (e.g., polystyrenesulfonic acid), or gelatin derivatives (e.g., aliphatic acylated gelatin, aromatic acylated gelatin and aromatic carbamoylated gelatin) may be used.

Silver halide emulsions are usually chemically sensitized. for this chemical sensitization, for example, the methods as described in H. Frieser ed., *Die Grundlagen Der Photographischen Prozesse mit Silberhalogeniden*, Akademische Verlagsgesellschaft, pages 675 to 734 (1968) can be used. Namely, a sulfur sensitization process using active gelatin or compounds (e.g., thiosulfates, thioureas, mercapto compounds and rhodanines) containing sulfur capable of reacting with silver; a reduction sensitization process using reducing substances (e.g., stannous salts, amines, hydrazine derivatives, formamidinesulfinic acid, and silane compounds); a noble metal sensitization process using noble metal compounds (e.g., complex salts of Group VIII metals in the Periodic Table, such as Pt, Ir and Pd, etc., as well as gold complex salts); and so forth can be applied alone or in combination with each other.

The photographic emulsion used in the present invention may include various compounds for the purpose of preventing fog formation or of stabilizing photographic performance in the photographic light-sensitive material during the production, storage or photographic processing thereof. For example, those compounds known as antifoggants or stabilizers can be incorporated, including azoles such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (particularly 1-phenyl-5-mercaptotetrazole), etc.; mercaptopyrimidines; mercaptotriazines; thioketo compounds such as oxazolinethione, etc.; azaindenes such as triazaindenes, tetraazaindenes (particularly 4-hydroxy-substituted (1,3,3a,7)tetraazaindenes), pentaazaindenes, etc.; benzenethiosulfonic acids; benzenesulfinic acids; benzenesulfonic amides; etc.

In the photographic emulsion layers or other hydrophilic colloid layers of the photographic light-sensitive material of the present invention can be incorporated various surface active agents as coating aids or for other various purposes, e.g., prevention of charging, improvement of slipping properties, acceleration of emulsification and dispersion, prevention of adhesion, and improvement of photographic characteristics (for example, development acceleration, high contrast, and sensitization), etc.

Surface active agents which can be used are nonionic surface active agents, e.g., saponin (steroid-based), alkylene oxide derivatives (e.g., polyethylene glycol, a polyethylene glycol/polypropylene glycol condensate, polyethylene glycol alkyl ethers or polyethylene glycol alkylaryl ethers, polyethylene glycol esters, polyethylene glycol sorbitan esters, polyalkylene glycol alkylamines or polyalkylene glycol alkylamides, and silicone/polyethylene oxide adducts, etc.), glycidol derivatives (e.g., alkenylsuccinic acid polyglyceride and alkylphenol polyglyceride, etc.), fatty acid esters of polyhydric alcohols, and alkyl esters of sugar, etc.; anionic surface active agents containing an acidic group, such as a carboxy group, a sulfo group, a phospho group, a sulfuric acid, ester group, and a phosphoric acid ester group, for example, alkylcarboxylic acid salts, alkylsulfonic acid salts, alkylbenzenesulfonic acid salts, alkylnaphthalenesulfonic acid salts, alkylsulfuric acid esters, alkylphosphoric acid esters, N-acyl-N-alkyltaurines, sulfosuccinic acid esters, sulfoalkylpolyoxyethylene alkylphenyl ethers, and polyoxyethylene alkylphosphoric acid esters; amphoteric surface active agents, such as amino acids, aminoalkylsulfonic acids, aminoalkylsulfuric acid or aminoalkylphosphoric acid esters, alkylbetaines, and amine oxides; and cationic surface active agents, e.g., alkylamine salts, aliphatic or aromatic quaternary ammonium salts, heterocyclic quaternary ammonium salts (e.g., pyridinium and imidazolium), and aliphatic or heterocyclic phosphonium or sufonium salts.

The photographic emulsion layer of the photograhic light-sensitive material of the present invention may contain compounds such as polyalkylene oxide or its ether, ester, amine or like derivatives, thioether compounds, thiomorpholines, quaternary ammonium salt compounds, urethane derivatives, urea derivatives, imidazole derivatives, and 3-pyrazolidones for the purpose of increasing sensitivity or contrast, or of accelerating development.

In the photographic emulsion layer or other hydrophilic colloid layers of the photographic light-sensitive material of the present invention can be incorporated water-insoluble or sparingly soluble synthetic polymer dispersions for the purpose of improving dimensional stability, etc. Synthetic polymers which can be used include homo- or copolymers of alkyl acrylate or methacrylate, alkoxyalkyl acrylate or methacrylate, glycidyl acrylate or methacrylate, acrylamide or methacrylamide, vinyl esters (e.g., vinyl acetate), acrylonitrile, olefins, styrene, etc. and copolymers of the foregoing monomers and acrylic acid, methacrylic acid, $\alpha,\beta$-unsaturated dicarboxylic acid, hydroxyalkyl acrylate or methacrylate, sulfoalkyl acrylate or methacrylate, and styrenesulfonic acid, etc.

In photographic processing of layers composed of photographic emulsions in the photographic light-sensitive material of the present invention, any of known procedures and known processing solutions, e.g., those described in *Research Disclosure*, No. 176, pages 28 to 30 can be used. The processing temperature is usually chosen from between 18° C. and 50° C., although it may be lower than 18° C. higher than 50° C.

Any fixing solutions which have compositions generally used can be used in the present invention. As fixing agents, thiosulfuric acid salts and thiocyanic acid salts, and in addition, organic sulfur compounds which are known to be effective as fixing agents can be used. These fixing solutions may contain water-soluble aluminum salts as hardeners.

Color developing solutions are usually alkaline aqueous solutions containing color developing agents. As these color developing agents, known primary aromatic amine developing agents, e.g., phenylenediamines such as 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfonamidoethylaniline, 4-amino-3-methyl-N-ethyl-N-$\beta$-methoxyethylaniline, etc., can be used.

In addition, the compounds as described in L.F.A. Mason, *Photographic Processing Chemistry*, Focal Press, pages 226 to 229 (1966), U.S. Pat. Nos. 2,193,015 and 2,592,364, Japanese Patent Application (OPI) No. 64933/73, etc., may be used.

The color developing solutions can further contain pH buffering agents such as sulfite, carbonates, borates and phosphates of alkali metals, etc. developing inhibitors or anti-fogging agents such as bromides, iodides or organic anti-fogging agents, etc. In addition, if desired, the color developing solutions can also contain water softeners; preservatives such as hydroxylamine, etc.; organic solvents such as benzyl alcohol, diethylene glycol, etc.; developing accelerators such as polyethylene glycol, quaternary ammonium salts, amines, etc.; dye forming couplers; competing couplers; fogging agents such as sodium borohydride, etc.; auxiliary developing agents such as 1-phenyl-3-pyrazolidone, etc.; viscosity-imparting agents; polycarboxylic acid type chelating agents; anti-oxidizing agents; and the like.

After color development, the photographic emulsion layer is usually bleached. This bleach processing may be performed simultaneously with a fix processing, or they may be performed independently.

Bleaching agents which can be used include compounds of polyvalent metals, e.g., iron (III), cobalt (III), chromium (VI), and copper (II), peracids, quinones and nitroso compounds. For example, ferricyanides; dichromates; organic complex salts of iron (III) or cobalt (III), e.g., complex salts of aminopolycarboxylic acids (e.g., ethylenediaminetetraacetic acid, nitrilotriacetic acid, 1,3-diamino-2-propanoltetraacetic acid, etc.) or organic acids (e.g., citric acid, tartaric acid, malic acid, etc.); persulfates; permanganates; nitrosophenol, etc. can be used. Of these compounds, potassium ferricyanide, iron (III) sodium ethylenediaminetetraacetate, and iron (III) ammonium ethylenediaminetetraacetate are particularly useful. Ethylenediaminetetraacetic acid iron (III) complex salts are useful in both an independent bleaching solution and a mono-bath bleach-fixing solution.

The photographic emulsion used in the present invention can also be spectrally sensitized with methine dyes or other dyes. Suitable dyes which can be employed include cyanine dyes, merocyanine dyes, complex cyanine dyes, complex merocyanine dyes, holopolar cyanine dyes, hemicyanine dyes, styryl dyes, and hemioxonol dyes. Of these dyes, cyanine dyes, merocyanine dyes and complex merocyanine dyes are particularly useful.

Any conventionally utilized nuclei for cyanine dyes are applicable to these dyes as basic heterocyclic nuclei. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc., and further, nuclei formed by condensing alicyclic hydrocarbon rings with these nuclei and nuclei formed by condensing aromatic hydrocarbon rings with these nuclei, that is, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc., are appropriate. The carbon atoms of these nuclei can also be substituted.

The merocyanine dyes and the complex merocyanine dyes that can be employed contain 5- or 6-membered heterocyclic nuclei such as a pyrazolin-5-one nucleus, a thiohydantoin nucleus, a 2-thioxazolidin-2,4-dione nucleus, a thiazolidine-2,4-dione nucleus, a rhodanine nucleus, a thiobarbituric acid nucleus, and the like.

These sensitizing dyes can be employed individually, and can also be employed in combination. A combination of sensitizing dyes is often used particularly for the purpose of supersensitization.

The sensitizing dyes may be present in the emulsion together with dyes which themselves do not give rise to spectrally sensitizing effects but exhibit a supersensitizing effect or materials which do not substantially absorb visible light but exhibit a supersensitizing effect. For example, aminostilbene compounds substituted with a nitrogen-containing heterocyclic group (e.g., those described in U.S. Pat. Nos. 2,933,390 and 3,635,721), aromatic organic acid-formaldehyde condensates (e.g., those described in U.S. Pat. No. 3,743,510), cadmium salts, azaindene compounds, and the like, can be present.

The present invention is also applicable to a multi-layer multicolor photographic material containing layers sensitive to at least two different spectral wavelength ranges on a support. A multi-layer natural color photographic material generally possesses at least one red-sensitive silver halide emulsion layer, at least one green-sensitive silver halide emulsion layer and at least one blue-sensitive silver halide emulsion layer, respectively, on a support. The order of these layers can be varied, if desired. Ordinarily, a cyan forming coupler is present in a red-sensitive emulsion layer, a magenta forming coupler is present in a green-sensitive emulsion layer and a yellow forming coupler is present in a blue-sensitive emulsion layer, respectively. However, if desired, a different combination can be employed.

The same or different photographic emulsion layers or light-insensitive layers of the photographic light-sensitive material of the present invention can be incorporated, in addition to the compounds according to the present invention described above, with other dye forming couplers, e.g., compounds capable of forming color upon oxidative coupling with aromatic primary amine developing agents (e.g., phenylenediamine derivatives, aminophenol derivatives, etc.) during the course of color development processing. Examples of such couplers include magenta couplers, such as 5-pyrazolone couplers, pyrazolobenzimidazole couplers, pyrazoloimidazole couplers, pyrazolopyrazole couplers, pyrazolotriazole couplers, pyrazolotetrazole couplers, cyanoacetyl coumarone couplers and open chain acylacetonitrile couplers, etc.; yellow couplers, such as acylacetamide couplers (e.g., benzoylacetanilides, pivaloylacetanilides, etc.), etc.; and cyan couplers, such as naphthol couplers and phenol couplers, etc. It is preferable to use non-diffusible couplers containing a hydrophobic group (so-called ballast group) within the molecule or polymeric couplers. They may be either 4-equivalent or 2-equivalent with respect to silver ions. It is also possible to use colored couplers capable of exerting color correction effects, or couplers capable of releasing development inhibitors during the course of development (so-called DIR couplers).

Further, the emulsion layer may contain non-color-forming DIR coupling compounds which release a development inhibitor, the product of which formed by a coupling reaction is colorless, other than DIR couplers.

Moreover, the photographic light-sensitive material may contain compounds which release a development inhibitor during the course of development, other than DIR couplers.

Two or more kinds of the compounds according to the present invention and the above-described couplers and the like can be incorporated together in the same layer for the purpose of satisfying the properties required of the photographic light-sensitive material, or the same compound can naturally be added to two or more layers.

The photographic light-sensitive material of the present invention may contain inorganic or organic hardeners in the photographic emulsion layer and other hydrophilic colloid layers thereof. For example, chromium salts (e.g., chromium alum, chromium acetate, etc.), aldehydes (e.g., formaldehyde, glyoxal, glutaraldehyde, etc.), N-methylol compounds (e.g., dimethylolurea, methyloldimethylhydantoin, etc.), dioxane derivatives (e.g., 2,3-dihydroxydioxane, etc.), active vinyl compounds (e.g., 1,3,5-triacryloylhexahydro-s-triazine, 1,3-vinylsulfonyl-2-propanol, etc.), active halogen compounds (e.g., 2,4-dichloro-6-hydroxy-s-triazine, etc.), and mucohalogenic acids (e.g., mucochloric acid, mucophenoxychloric acid, etc.) can be used alone or in combination with each other.

In the photographic light-sensitive material of the invention, when dyes, ultraviolet ray absorbing agents, and the like are incorporated in the hydrophilic colloid layers, they may be mordanted with cationic polymers, etc.

The photographic light-sensitive material of the present invention may contain therein hydroquinone derivatives, aminophenol derivatives, gallic acid derivatives, ascorbic acid derivatives, etc., as color fog preventing agents.

The hydrophilic colloid layers of the photographic light-sensitive material of the present invention can contain ultraviolet ray absorbing agents. For example, benzotriazole compounds substituted with aryl groups (e.g., those described in U.S. Pat. No. 3,533,794), 4-thiazolidone compounds (e.g., those described in U.S. Pat. Nos. 3,314,794 and 3,352,681), benzophenone compounds (e.g., those described in Japanese Patent Application (OPI) No. 2784/71), cinnamic acid ester compounds (e.g., those described in U.S. Pat. Nos. 3,705,805 and 3,707,375), butadiene compounds (e.g., those described in U.S. Pat. No. 4,045,229) or benzoxazole compounds (e.g., those described in U.S. Pat. No. 3,700,455) can be employed. Ultraviolet ray absorbing couplers (e.g., α-naphthol type cyan dye forming couplers) and ultraviolet ray absorbing polymers can also be employed. These ultraviolet ray absorbing agents can also be mordanted in a specific layer(s), if desired.

The photographic light-sensitive material of the present invention may contain water-soluble dyes in the hydrophilic colloid layers thereof as filter dye or for various purposes, e.g., irradiation prevention. Examples of such dyes include oxonol dyes, hemioxonol dyes, styryl dyes, merocyanine dyes, cyanine dyes, and azo dyes. In particular, oxonol dyes, hemioxonol dyes, and merocyanine dyes are useful.

In carrying out the present invention, known color fading preventing agents as described below can be used together. Color image stabilizers can be used alone or in combination with each other. Typical known color fading preventing agents include hydroquinone derivatives, gallic acid derivatives, p-alkoxyphenols, p-oxyphenol derivatives, and bisphenols, etc.

The present invention will be explained in greater detail with reference to the following examples, but the present invention should not be construed as being limited thereto. Unless otherwise specified, all parcents, ratios, etc. are by weight.

EXAMPLE 1

On a cellulose triacetate film support were coated layers having the compositions set forth below to prepare a multilayer color photographic light-sensitive material.

First Layer: Antihalation Layer

A gelatin layer containing black colloidal silver.

Second Layer: Intermediate Layer

A gelatin layer containing a dispersion of 2,5-di-tert-octylhydroquinone.

Third Layer: First Red-Sensitive Emulsion Layer

A silver iodobromide emulsion (iodide content: 5 mol%), silver coated amount: 1.6 g/m$^2$.
Sensitizing Dye I: $4.5 \times 10^{-4}$ mol per mol of silver
Sensitizing Dye II: $1.5 \times 10^{-4}$ mol per mol of silver
Coupler EX-1: 0.03 mol per mol of silver
Coupler EX-3: 0.03 mol per mol of silver

Fourth Layer: Second Red-Sensitive Emulsion Layer

A silver iodobromide emulsion (iodide content: 10 mol%), silver coated amount: 1.4 g/m$^2$.
Sensitizing Dye I: $3 \times 10^{-4}$ mole per mol of silver
Sensitizing Dye II: $1 \times 10^{-4}$ mol per mol of silver
Coupler EX-1: 0.002 mol per mol of silver
Coupler EX-2: 0.02 mol per mol of silver
Coupler EX-3: 0.0016 mol per mol of silver

Fifth Layer: Intermediate Layer

Same as the Second Layer.

Sixth Layer: First Green-Sensitive Emulsion Layer

A silver iodobromide emulsion (iodide content: 6 mol%), silver coated amount: 1.5 g/m$^2$.
Sensitizing Dye III: $5 \times 10^{-4}$ mol per mol of silver
Sensitizing Dye IV: $2 \times 10^{-4}$ mol per mol of silver
Coupler EX-4: 0.05 mol per mol of silver
Coupler EX-5: 0.003 mol per mol of silver
Coupler EX-9: 0.0015 mol per mol of silver

Seventh Layer: Second Green-Sensitive Emulsion Layer

A silver iodobromide emulsion (iodide content: 8 mol%), silver coated amount: 1.3 g/m$^2$.
Sensitizing Dye III: $3 \times 10^{-4}$ mol per mol of silver
Sensitizing Dye IV: $1.2 \times 10^{-4}$ mol per mol of silver
Coupler EX-7: 0.017 mol per mol of silver
Coupler EX-6: 0.003 mol per mol of silver

Eighth Layer: Yellow Filter Layer

A gelatin layer containing yellow colloidal silver and a dispersion of 2,5-di-tert-octylhydroquinone.

Ninth Layer: First Blue-Sensitive Emulsion Layer

A silver iodobromide emulsion (iodide content: 6 mol%), silver coated amount: 0.7 g/m$^2$.
Coupler EX-8: 0.25 mol per mol of silver
Coupler EX-9: 0.015 mol per mol of silver

Tenth Layer: Second Blue-Sensitive Emulsion Layer

A silver iodobromide emulsion (iodide content: 6 mol%), sliver coated amount: 0.6 g/m$^2$.
Coupler EX-8: 0.06 mol per mol of silver

Eleventh Layer: First Protective Layer

A gelatin layer containing silver iodobromide (iodide content: 1 mol%, average particle size: 0.07μ, silver coated amount: 0.5 g/m$^2$) and a dispersion of Ultraviolet Ray Absorbing Agent UV-1.

Twelfth Layer: Second Protective Layer

A gelatin layer containing polymethyl methacrylate particles (having a diameter of about 1.5μ)

Gelatin Hardener H-1 and a surface active agent were incorporated into each of the layers in addition to the above-described components.

The sample thus-prepared was designated Sample 101.

Preparation of Samples 102 to 110

Samples 102 to 110 were prepared in the same manner as described for Sample 101 except changing Coupler EX-9 used in the first green-sensitive emulsion layer to the compounds as shown in Table 1 below, respectively.

The structures of the compounds used for preparing these samples are as follows:

-continued
EX-3
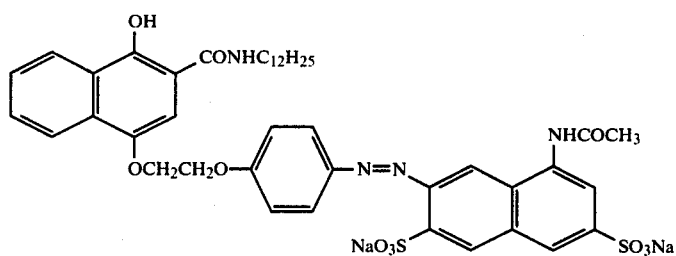
EX-4
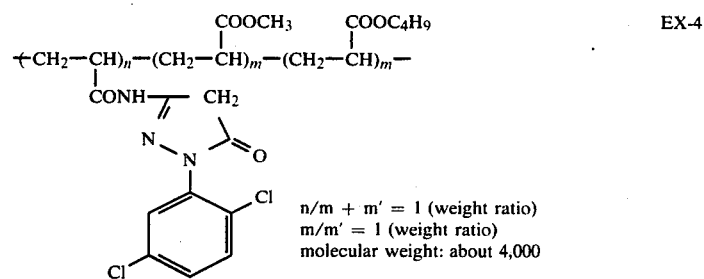
n/m + m' = 1 (weight ratio)
m/m' = 1 (weight ratio)
molecular weight: about 4,000
EX-5
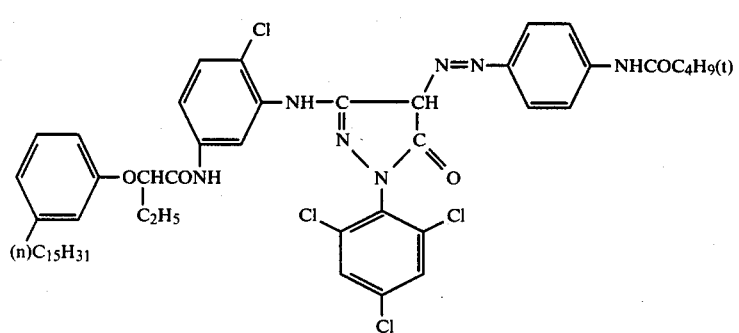
EX-6
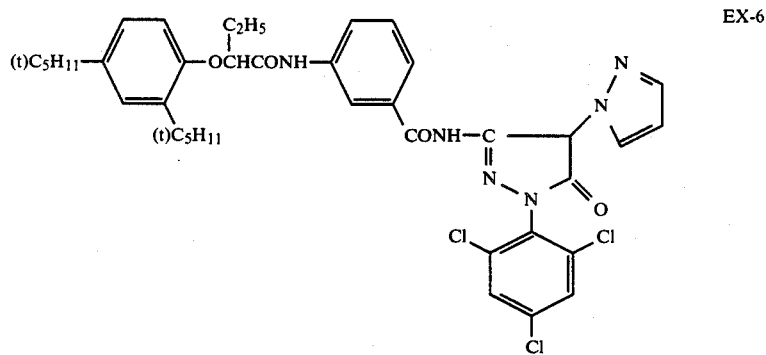
EX-7
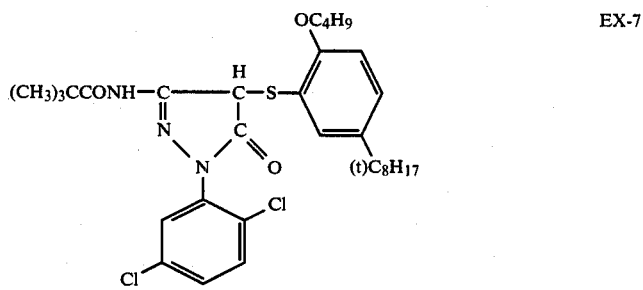

EX-8
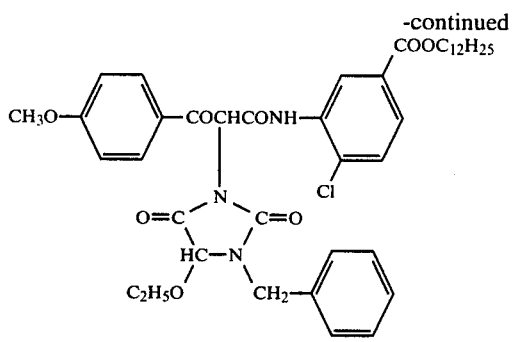
EX-9
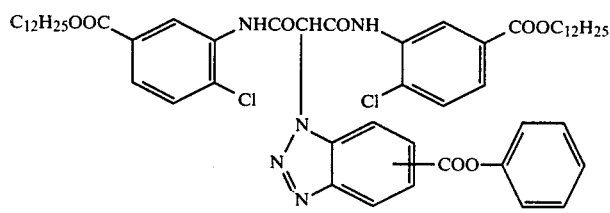
H-1
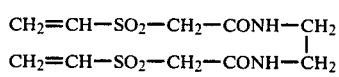
UV-1
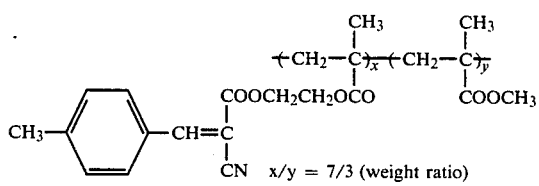
Sensitizing Dye I
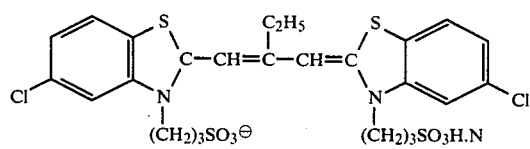
Sensitizing Dye II
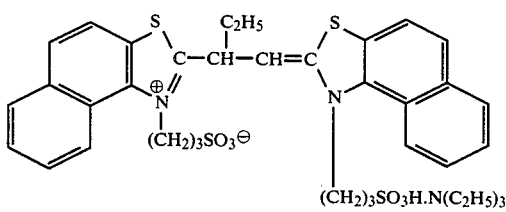
Sensitizing Dye III
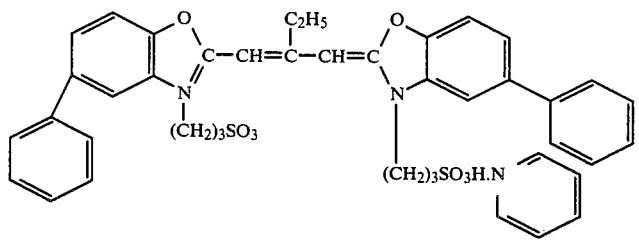
Sensitizing Dye IV
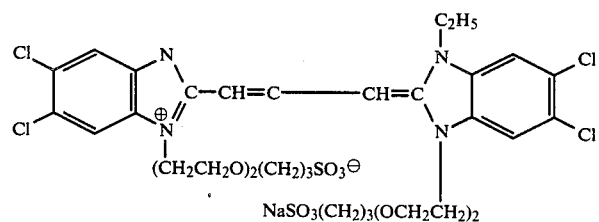

-continued

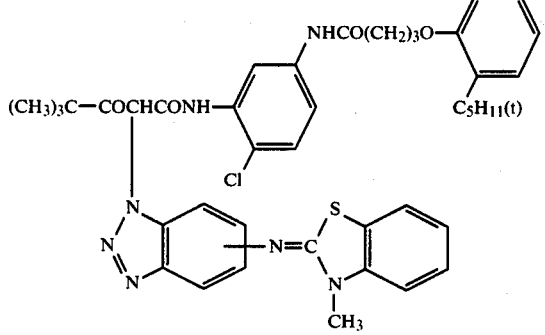
EX-10

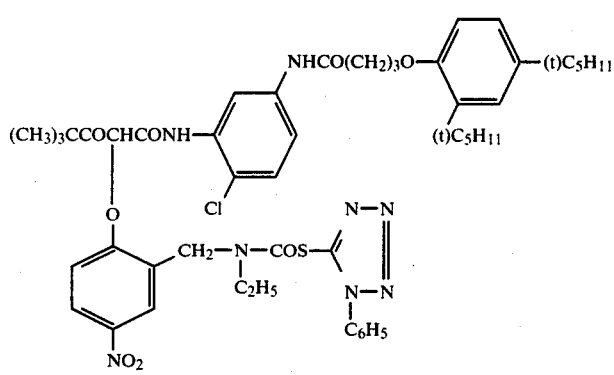
EX-11

Samples 101 to 110 were subjected to wedge exposure to white light and then development processing at 33° C. according to the following processing steps.

| Processing Steps | Time |
|---|---|
| 1. Color development | 3 min and 15 sec |
| 2. Bleaching | 6 min and 30 sec |
| 3. Washing with water | 3 min and 15 sec |
| 4. Fixing | 6 min and 30 sec |
| 5. Washing with water | 3 min and 15 sec |
| 6. Stabilizing | 3 min and 15 sec |

The composition of each processing solution used in the above-described processing is as follows.

| Color Developing Solution | |
|---|---|
| Sodium nitrilotriacetate | 1.0 g |
| Sodium sulfite | 4.0 g |
| Sodium carbonate | 30.0 g |
| Potassium bromide | 1.4 g |
| Hydroxylamine sulfate | 2.4 g |
| 4-(N—Ethyl-N—β-hydroxyethylamino)-2-methylaniline sulfate | 4.5 g |
| Water to make | 1 liter |
| Bleaching Solution | |
| Ammonium bromide | 160.0 g |
| Aqueous ammonia (28%) | 25.0 ml |
| Sodium ethylenediaminetetra-acetato iron (III) | 130.0 g |
| Glacial acetic acid | 14.0 ml |
| Water to make | 1 liter |
| Fixing Solution | |
| Sodium tetrapolyphosphate | 2.0 g |
| Sodium sulfite | 4.0 g |
| Ammonium thiosulfate aqueous solution (70%) | 175.0 ml |
| Sodium bisulfite | 4.6 g |
| Water to make | 1 liter |

| -continued | |
|---|---|
| Color Developing Solution | |
| Stabilizing Solution | |
| Formalin | 8.0 ml |
| Water to make | 1 liter |

The samples thus-processed exhibited almost the same sensitivity and gradation. The sharpness of the green-sensitive layers of these samples were evaluated using conventional MTF values at spatial frequencies of 4 cycles/mm and 40 cycles/mm. The results obtained are shown in Table 1 below.

TABLE 1

| Sample | Compound Added* to First Green-Sensitive Layer | Amount** Added | MTF Value 4 cycles/mm | MTF Value 40 cycles/mm |
|---|---|---|---|---|
| 101 (Comparison) | EX-9 | 1.0 | 1.10 | 0.42 |
| 102 (Comparison) | EX-10 | 1.0 | 1.04 | 0.38 |
| 103 (Comparison) | EX-11 | 2.5 | 1.08 | 0.45 |
| 104 (Present Invention) | (7) | 2.0 | 1.15 | 0.49 |
| 105 (Present Invention) | (8) | 3.0 | 1.18 | 0.53 |
| 106 (Present Invention) | (9) | 3.0 | 1.18 | 0.55 |
| 107 (Present Invention) | (6) | 2.0 | 1.16 | 0.52 |
| 108 (Present Invention) | (13) | 2.5 | 1.17 | 0.55 |

TABLE 1-continued

| Sample | Compound Added* to First Green-Sensitive Layer | Amount** Added | MTF Value 4 cycles/mm | MTF Value 40 cycles/mm |
|---|---|---|---|---|
| 109 (Present Invention) | (1) | 2.5 | 1.15 | 0.58 |
| 110 (Present Invention) | (2) | 2.5 | 1.14 | 0.57 |

*Compound added in place of Coupler EX-9 to the first green-sensitive emulsion layer.
**Amount added is indicated using a molar ratio taking the mole of Coupler EX-9 added as 1.

From the results shown in Table 1 above, it is understood that the MTF values in case of using the compounds according to the present invention are extremely high in comparison with the case of using the conventional DIR couplers. The effects according to the present invention are clearly demonstrated.

EXAMPLE 2

On a polyethylene terephthalate film support were coated layers having the compositions set forth below to prepare a multilayer color photographic light-sensitive material.

First Layer: Antihalation Layer

A gelatin layer containing black colloidal silver.

Second Layer: Intermediate Layer

A gelatin layer containing a dispersion of 2,5-ditert-octygydroquinone.

Third Layer: Red-Sensitive Emulsion Layer

A silver iodobromide emulsion (iodide content: 7 mol%), silver coated amount: 2.0 g/m².
Sensitizing Dye I: $4.5 \times 10^{-4}$ mol per mol of silver
Sensitizing Dye II: $1.5 \times 10^{-4}$ mol per mol of silver
Coupler EX-1: 0.04 mol per mol of silver
Coupler EX-3: 0.003 mol per mol of silver
Coupler EX-9: 0.004 mol per mol of silver
Tricresyl Phosphate: 0.5 g/m²
Dibutyl Phthalate: 0.2 g/m²

Fourth Layer: First Protective Layer

A gelatin layer containing silver iodobromide (iodide content: 1 mol%, average particle size: 0.07μ, silver coated amount: 0.5 g/m²) and a dispersion of Ultraviolet Ray Absorbing Agent UV-1.

Fifth Layer: Second Protective Layer

A gelatin layer containing polymethyl methacrylate particles (having a diameter of about 1.5μ).

Gelatin Hardener H-1 and a surface active agent were incorporated into each of the layers in addition to the above-described components.

The sample thus-prepared was designated Sample 111.

Preparation of Samples 112 to 119

Samples 112 to 119 were prepared in the same manner as described for Sample 111 except changing Coupler EX-9 used in the green-sensitive emulsion layer to the compounds as shown in Table 2 below, respectively.

The structures of the compounds used for preparing these samples are same as those described in Example 1, except Coupler EX-12 which has the following structure.

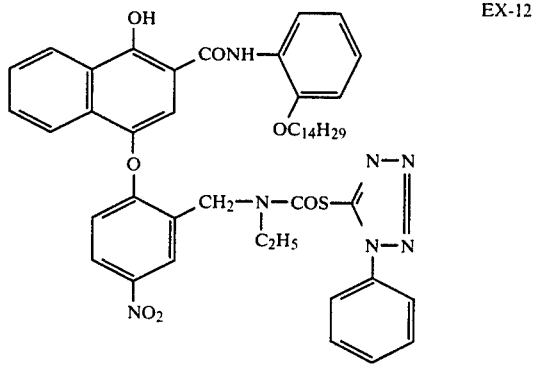

EX-12

Samples 111 to 119 were subjected to wedge exposure to white light and then development processing in the same manner as described in Example 1. The samples thus-processed exhibited almost the same sensitivity and gradation. The MTF values at spatial frequencies of 4 cycles/mm and 40 cycles/mm were measured with these samples. The results obtained are shown in Table 2 below.

TABLE 2

| Sample | DIR Coupler Used | Amount Added | MTF Value 4 cycles/mm | MTF Value 40 cycles/mm |
|---|---|---|---|---|
| 111 (Comparison) | EX-9 | 1.0 | 1.15 | 0.63 |
| 112 (Comparison) | EX-11 | 2.5 | 1.18 | 0.67 |
| 113 (Comparison) | EX-12 | 1.5 | 1.13 | 0.65 |
| 114 (Present Invention) | (1) | 2.5 | 1.27 | 0.73 |
| 115 (Present Invention) | (2) | 2.5 | 1.25 | 0.74 |
| 116 (Present Invention) | (3) | 3.0 | 1.28 | 0.77 |
| 117 (Present Invention) | (11) | 3.0 | 1.25 | 0.75 |
| 118 (Present Invention) | (12) | 2.5 | 1.29 | 0.78 |
| 119 (Present Invention) | (30) | 1.5 | 1.20 | 0.70 |

From the results shown in Table 2 above, it is understood that the MFT values are extremely high in case of using the compounds according to the present invention in comparison with the case of using the conventional DIR couplers. The effects according to the present invention are clearly demonstrated.

EXAMPLE 3

In order to examine preservability of the films used in Example 2, Samples 113 to 116 were stored at room temperature for 3 days or at 45° C. and 80% RH for 3 days and then subjected to wedge exposure to white light and development processing at 20° C. according to the following processing steps.

| Processing Step | Time |
|---|---|
| 1. Development | 10 min |
| 2. Stopping | 1 min |
| 3. Fixing | 5 min |
| 4. Washing with water | 10 min |

The composition of each processing solution used in the above-described processing is as follows.

| Developing Solution | |
|---|---|
| Sodium Sulfite | 33 g |
| Metal | 3 g |
| Hydroquinone | 3 g |
| Sodium carbonate (monohydrate) | 23 g |
| Potassium bromide | 1.7 g |
| Water to make | 1 liter |
| Stopping Solution | |
| Glacial acetic acid | 15 ml |
| Water to make | 1 liter |
| Fixing Solution | |
| Sodium thiosulfate | 191 g |
| Sodium sulfite | 20 g |
| Glacial acetic acid | 20 ml |
| Water to make | 1 liter |

The samples thus-processed were subjected to sensitometry. The results obtained are shown in Table 3 below.

TABLE 3

| Sample | DIR Coupler Used | Relative Sensitivity* (%) |
|---|---|---|
| Blank | none | 98 |
| 113 (Comparison) | EX-12 | 73 |
| 114 (Present Invention) | (1) | 98 |
| 115 (Present Invention) | (2) | 98 |
| 116 (Present Invention) | (3) | 98 |

*Relative sensitivity of the sample stored at 45° C. and 80% RH for 3 days to the sample stored at room temperature for 3 days.

From the results shown in Table 3 above, it is apparent that the compounds according to the present invention do not release development inhibitors upon hydrolysis during the preservation and thus do not cause any decrease in sensitivity. The effects of the present invention are dearly demonstrated.

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material comprising a support having thereon at least one silver halide emulsion layer, the color photographic light-sensitive material containing a compound represented by the general formula (Ia):

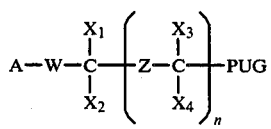

(Ia)

wherein W, Z, $X_1$, $X_2$, $X_3$, $X_4$, n and PUG are as defined below and A represents a coupler residue or a hydroquinone residue which releases a group represented by the general formula (I) described below upon reaction with the oxidation product of a developing agent:

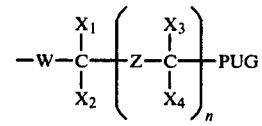

(I)

wherein W and Z each represents an oxygen atom, a sulfur atom or a group of

$X_1$, $X_2$, $X_3$, $X_4$ and $X_5$ each represents a hydrogen atom or an organic residue; PUG represents a photographically useful group which is bonded to

via a hetero atom of PUG and is released as an anion following release of the groups represented by the general formula (I); n represents 1 or 2; any two of $X_1$, $X_2$, $X_3$, $X_4$, $X_5$ and PUG each represents a divalent group and may be connected to each other to form a cyclic structure; and when n represents 2, two Z's, two $X_3$'s and two $X_4$'s each may be the same or different.

2. A silver halide color photographic light-sensitive material as claimed in claim 1, wherein the compound represented by the formula (Ia) is present in one of the at least one silver halide emulsion layer.

3. A silver halide color photographic light-sensitive material as claimed in claim 1, wherein the group represented by the general formula (Ia) is connected to the coupling position of a coupler residue directly or through a timing group.

4. A silver halide color photographic light-sensitive material as claimed in claim 1, wherein the photographic light-sensitive material further contains a color forming coupler capable of forming a dye upon the reaction with the oxidation product of a developing agent.

5. A silver halide color photographic light-sensitive material as claimed in claim 1, wherein A represents a coupler residue.

6. A silver halide color photographic light-sensitive material as claimed in claim 1, wherein A represents a yellow color image forming coupler residue selected from the group consisting of a pivaloyl acetanilide group, a benzoyl acetanilide group, a malonic diester group, a malondiamide group, a dibenzoylmethane group, a benzothiazolyl acetamide group, a malonic ester monoamide group, a benzothiazolyl acetate group, a benzoxazolyl acetamide group, a benzoxazolyl acetate group, a benzimidazolyl acetamide group and a benzimidazolyl acetate group.

7. A silver halide color photographic light-sensitive material as claimed in claim 1, wherein A represents a magenta color image forming coupler residue selected from the group consisting of a 5-oxo-2-pyrazoline group, pyrazolobenzimidazole group, a pyrazolotriazole group, a cyanoacetophenone group and a pyrazoloimidazole group.

8. A silver halide color photographic light-sensitive material as claimed in claim 1, wherein A represents a cyan color image forming coupler residue selected from the group consisting of a phenol group and an α-naphthol group.

9. A silver halide color photographic light-sensitive material as claimed in claim 1, wherein A represents a non-color forming coupler residue selected from the group consisting of an indanone group and an acetophenone group.

10. A silver halide color photographic light-sensitive material as claimed in claim 1, wherein the group represented by PUG is a group containing a development inhibitor, a development accelerator, a fogging agent, a dye, a developing agent, a coupler, a silver removing accelerator, a silver halide solvent, a competing compound or a silver removing inhibitor.

11. A silver halide color photographic light-sensitive material as claimed in claim 10, wherein the group represented by PUG is a group represented by the following general formula (P-1), (P-2), (P-3), (P-4), (P-5), (P-6), (P-7), (P-8) or (P-9):

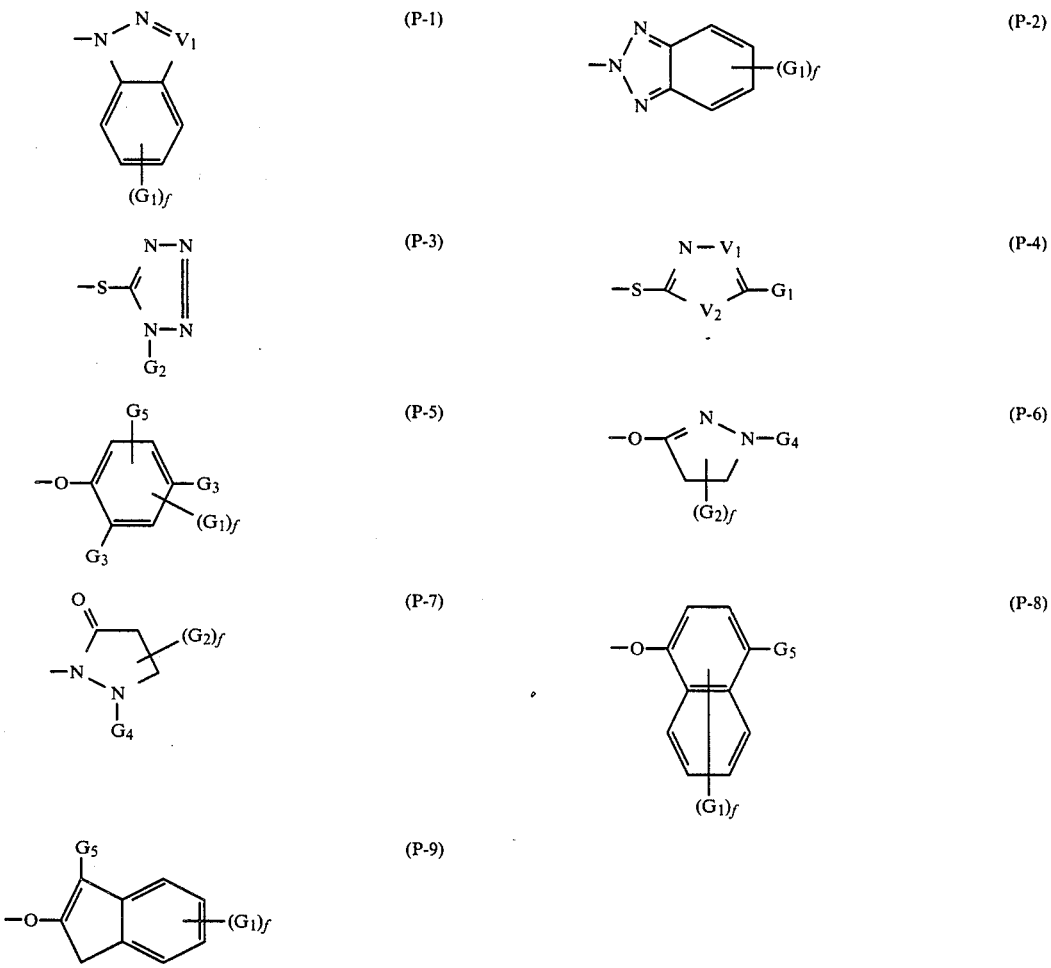

wherein $G_1$ represents a hydrogen atom, a halogen atom, an alkyl group, an acylamino group, an alkoxy group, a sulfonamido group, an aryl group, an alkylthio group, an alkylamino group, an anilino group, an amino group, an alkoxycarbonyl group, an acyloxy group, a nitro group, a cyano group, a sulfonyl group, an aryloxy group, a hydroxy group, a thioamido group, a carbamoyl group, a sulfamoyl group, a carboxy group, a ureido group or an aryloxycarbonyl group; $G_2$ represents a hydrogen atom, an alkyl group or an aryl group; $G_3$ represents a hydroxy group, a sulfonamido group, an amino group, an alkylamino group, an anilino group or a hydrogen atom, two $G_3$'s in the general formula (P-5) may be the same or different provided that both $G_3$'s are not hydrogen atoms at the same time; $G_4$ represents an aryl group; $G_5$ represents a hydrogen atom, a heterocyclic thio group or a nitrogen-containing heterocyclic group condensed with a benzene ring; f represents an integer of 1 to 2, when f is 2, two $G_1$'s may be the same or different; $V_1$ represents a nitrogen atom or a group of $$-\underset{G_1}{\overset{}{\underset{|}{C}}}=$$

(wherein $G_1$ has the same meaning as defined above and may be the same or different from other $G_1$'s present in the molecule thereof); and $V_2$ represents an oxygen atom, a sulfur atom or a group of

(wherein G₂ has the same meaning as defined above), and in the general formula (p-4) when V₁ represents a group of

two G₁'s may be combined to form a condensed benzene ring.

12. A silver halide color photographic light-sensitive material as claimed in claim 1, wherein the organic residue represented by $X_1$, $X_2$, $X_3$ or $X_4$ is an alkyl group, an aryl group, an acyl group, a sulfonyl group, a carbamoyl group, a sulfamoyl group, an alkoxycarbonyl group, an aryloxycarbonyl group, an alkoxysulfonyl group, an aryloxysulfonyl group, a cyano group, a nitro group, a nitroso group, a carboxy group, a sulfo group, a thioacyl group, a thiocarbamoyl group or an imidoyl group.

13. A silver halide color photographic light-sensitive material as claimed in claim 1, wherein the organic residue represented by $X_5$ in the group of

which is represented by W or Z is an alkyl group, an aryl group, an acyl group, a sulfonyl group, carbamoyl group, a sulfamoyl group, an alkoxycarbonyl group, an aryloxycarbonyl group, an alkoxysulfonyl group, an aryloxysulfonyl group, a cyano group, a nitro group, a nitroso group, a carboxy group, a sulfo group, a thioacyl group, a thiocarbamoyl group or an imidoyl group.

14. A silver halide color photographic light-sensitive material as claimed in claim 1, wherein the cyclic structure formed with any two of $X_1$, $X_2$, $X_3$, $X_4$ and $X_5$ is a group represented by the following formula:

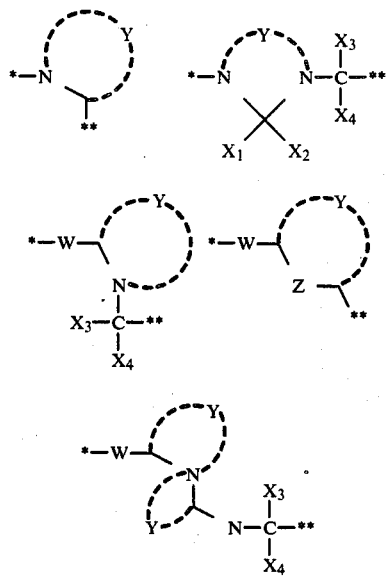

-continued

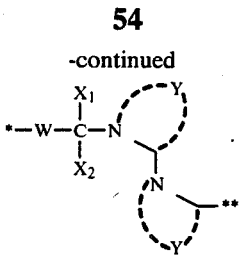

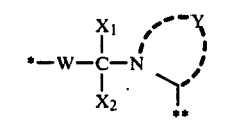

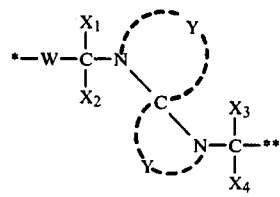

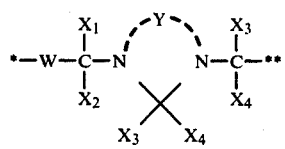

wherein a bond indicated by * denotes the position at which the group is connected to A; a bond indicated by ** denotes the position at which the group is connected to PUG; W, Z, $X_1$, $X_2$, $X_3$ and $X_4$ each has the same meaning as defined for the general formula (Ia); and Y represents a divalent organic residue necessary for forming a 4-membered, 5-membered or 6-membered ring.

15. A silver halide color photographic light-sensitive material as claimed in claim 14, wherein the divalent organic residue represented by Y is a group represented by the following general formula:

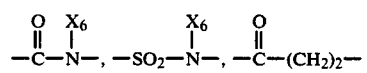

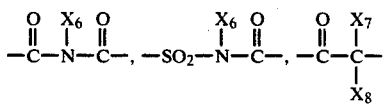

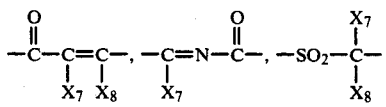

wherein $X_6$, $X_7$ and $X_8$ each represents a hydrogen atom, an alkyl group, an aryl group, an acyl group, a sulfonyl group, a carbamoyl group, a sulfamoyl group, an alkoxycarbonyl group, an aryloxycarbonyl group, an alkoxysulfonyl group, an aryloxysulfonyl group, a cyano group, a nitro group, a nitroso group, a carboxy group, a sulfo group, a thioacyl group, a thiocarbamoyl group or an imidoyl group.

16. A silver halide color photographic light-sensitive material as claimed in claim 1, wherein A represents a coupler residue represented by the following general formula (II) or (III):

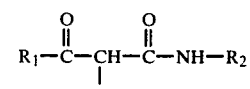

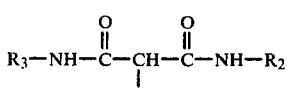

wherein $R_1$ represents an aliphatic group, an aromatic group, an alkoxy group or a heterocyclic group; and $R_2$ and $R_3$ each represents an aromatic group or a heterocyclic group.

17. A silver halide color photographic light-sensitive material as claimed in claim 16, wherein the aliphatic group represented by $R_1$ is an alkyl group which may be substituted with a substituent selected from an alkoxy group, an aryloxy group, an amino group, an acylamino group and a halogen atom.

18. A silver halide color photographic light-sensitive material as claimed in claim 16, wherein the aromatic group represented by $R_1$, $R_2$ or $R_3$ is a phenyl group which may be substituted with a substituent selected from the group consisting of an alkyl group, an alkenyl group, an alkoxy group, an alkoxycarbonyl group, an alkoxycarbonylamino group, an aliphatic amido group, an alkylsulfamoyl group, an alkylsulfonamido group, an alkylureido group, an alkyl-substituted succinimido group each containing 32 or less carbon atoms, an aryloxy group, an aryloxycarbonyl group, an arylcarbamoyl group, an arylamido group, an arylsulfamoyl group, an arylsulfonamido group, an arylureido group, an amino group, a hydroxy group, a carboxy group, a sulfo group, a nitro group, a cyano group, a thiocyano group and a halogen atom.

19. A silver halide color photographic light-sensitive material as claimed in claim 16, wherein the aromatic group represented by $R_1$, $R_2$ or $R_3$ is a naphthyl group, a quinolyl group, an isoquinolyl group, a chromanyl group, a coumaranyl group or a tetrahydronaphthyl group.

20. A silver halide color photographic light-sensitive material as claimed in claim 16, wherein the alkoxy group represented by $R_1$ is an alkoxy group in which the alkyl moiety represents a straight chain or branched chain alkyl group having from 1 to 32 carbon atoms, an alkenyl group, a cyclic alkyl group or a cyclic alkenyl group each of which may be substituted with a substituent selected from the group consisting of a halogen atom, an aryl group and an alkoxy group.

21. A silver halide color photographic light-sensitive material as claimed in claim 16, wherein the heterocyclic group represented by $R_1$, $R_2$ or $R_3$ is a group derived from a hetero ring selected from the group consisting of thiophene, furan, pyran, pyrrole, pyrazole, pyridine, pyrazine, pyrimidine, pyridazine, indolizine, imidazole, thiazole, oxazole, triazine, thiadiazole and oxazine.

22. A silver halide color photographic light-sensitive material as claimed in claim 1, wherein A represents a coupler residue represented by the following general formula (IV), (V), (VI) or (VII):

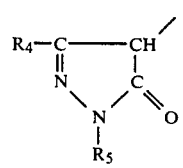

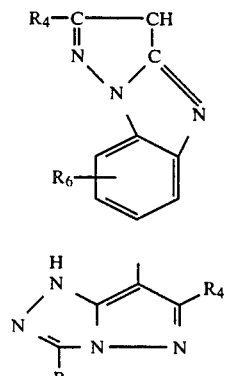

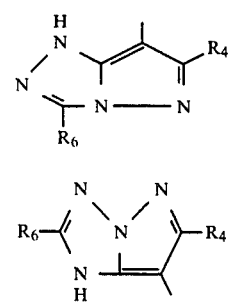

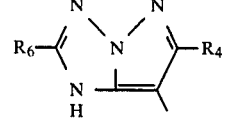

wherein $R_5$ represents a straight chain or branched chain alkyl group having from 1 to 32 carbon atoms, an alkenyl group, a cyclic alkyl group, an aralkyl group or a cyclic alkenyl group each of which may be substituted with a substituent selected from the group consisting of a halogen atom, a nitro group, a cyano group, an aryl group, an alkoxy group, an aryloxy group, a carboxy group, an alkylthiocarbonyl group, an arylthiocarbonyl group, an alkoxycarbonyl group, an aryloxycarbonyl group, a sulfo group, a sulfamoyl group, a carbamoyl group, an acylamino group, a diacylamino group, a ureido group, a urethane group, a thiourethane group, a sulfonamido group, a heterocyclic group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxy group and a mercapto group; an aryl group which may be substituted with a substituent selected from an alkyl group, an alkenyl group, a cyclic alkyl group, an aralkyl group, a cyclic alkenyl group, a halogen atom, a nitro group, a cyano group, an aryl group, an alkoxy group, an aryloxy group, a carboxy group, an alkoxycarbonyl group, an aryloxycarbonyl group, a sulfo group, a sulfamoyl group, a carbamoyl group, an acylamino group, a diacylamino group, a ureido group, a urethane group, a sulfonamido group, a heterocyclic group, an arylsulfonyl group, an alkylsulfonyl group, an arylthio group, an alkylthio group, an alkylamino group, a dialkylamino group, an anilino group, an N-alkylanilino group, an N-arylanilino group, an N-acylanilino group, a hydroxy group and a mercapto group; a heterocyclic group which may be substituted with a substituent selected from the group consisting of the substituents as defined for the above-described aryl group; an aliphatic acyl group; an aromatic acyl group; an alkylsulfonyl group; an arylsulfonyl group; an alkylcarbamoyl group; an arylcarbamoyl group; an alkylthiocarbamoyl group; or an arylthiocarbamoyl group; $R_4$ represents a hydrogen atom; a straight chain or branched chain alkyl group having from 1 to 32 carbon atoms, an alkenyl group, a cyclic alkyl group, an aralkyl group, a cyclic alkenyl group, an aryl group or a heterocyclic group each of which may be substituted with a substituent selected from the group consisting of the substituents as defined for these groups of $R_5$ respectively an alkoxycarbonyl group; an aryloxycarbonyl group; an aralkyloxycarbonyl group; an alkoxy group; an aryloxy group; an alkylthio group; an arylthio group; a carboxy group; an acylamino group; a diacylamino group; an N-alkylacylamino group; an N-arylacylamino group; a ureido group; a urethane group; a thiourethane group; an arylamino group; an alkylamino group; a cycloamino group; a heterocyclic amino group; an alkylcarbonyl group; an arylcarbonyl group; a sulfonamido group; a carbamoyl group; a sulfamoyl group; a cyano group; a hydroxy group; a mercapto group; a halogen atom; or a sulfo group; and $R_6$ represents a hydrogen atom, a straight chain or branched chain alkyl group having from 1 to 32 carbon atoms, an alkenyl group, a cyclic alkyl group, an aralkyl group, a cyclic alkenyl group, an aryl group or a heterocyclic group each of which may be substituted with a substituent selected from the group consisting of the substituents as defined for these groups of $R_5$ respectively; a cyano group; an alkoxy group, an aryloxy group, a halogen atom, a carboxy group, an alkoxycarbonyl group, an aryloxycarbonyl group, an acyloxy group, a sulfo group, a sulfamoyl group, a carbamoyl group, an acylamino group, a diacylamino group, a ureido group, a urethane group, a sulfonamido group, an arylsulfonyl group, an alkylsulfonyl group, an arylthio group, an alkylthio group, an alkylamino group, a dialkylamino group, an anilino group, an N-arylanilino group, an N-alkylanilino group, an N-acrylanilino group, a hydroxy group or a mercapto group.

23. A silver halide color photographic light-sensitive material as claimed in claim 22, wherein $R_5$ represents a phenyl group which is substituted with an alkyl group, an alkoxy group or a halogen atom at least at one of the positions.

24. A silver halide color photographic light-sensitive material as claimed in claim 1, wherein A represents a coupler residue represented by the following general formula (VIII), (IX) or (X):

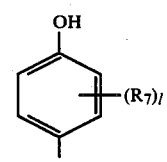
(VIII)

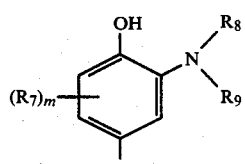
(IX)

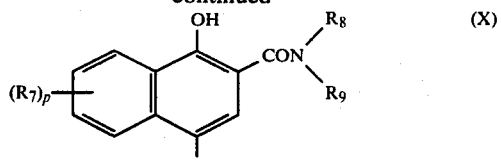
(X)

wherein $R_7$ represents a hydrogen atom, a halogen atom, an alkoxycarbonylamino group, an aliphatic hydrocarbon residue, an N-arylureido group, an acylamino group, an —O—$R_{12}$ group or an —S—$R_{12}$ group (wherein $R_{12}$ represents an aliphatic hydrocarbon residue); $R_8$ and $R_9$ each represents an aliphatic hydrocarbon residue, an aryl group or a heterocyclic group, one of $R_8$ and $R_9$ may be a hydrogen atom, or $R_8$ and $R_9$ may combine with each other to form a nitrogen-containing heterocyclic nucleus; l represents an integer of 1 to 4; m represents an integer of 1 to 3; and p represents an integer of 1 to 5.

25. A silver halide color photographic light-sensitive material as claimed in claim 24, wherein the aliphatic hydrocarbon group, the aryl group or the heterocyclic group represented by $R_7$, $R_8$ or $R_9$ may be substituted with a substituent selected from the group consisting of a halogen atom, a nitro group, a hydroxy group, a carboxy group, an amino group, a substituted amino group, a sulfo group, an alkyl group, an alkenyl group, an aryl group, a heterocyclic group, an alkoxy group, an aryloxy group, an arylthio group, an arylazo group, an acylamino group, a carbamoyl group, an ester group, an acyl group, an acyloxy group, a sulfonamido group, a sulfamoyl group, a sulfonyl group and a morpholino group.

26. A silver halide color photographic light-sensitive material as claimed in claim 1, wherein A represents a coupler residue represented by the following general formula (XI) or (XII)

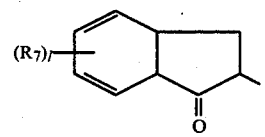
(XI)

(XII)

wherein $R_7$ represents a hydrogen atom, a halogen atom, an alkoxycarbonylamino group, a aliphatic hydrocarbon residue, an N-arylureido group, an acylamino group, an —O—$R_{12}$ group or an —S—$R_{12}$ group (wherein $R_{12}$ represents an aliphatic hydrocarbon residue); $R_{10}$ represents an arylcarbonyl group, an alkanoyl group having from 2 to 32 carbon atoms, an arylcarbamoyl group, an alkenecarbamoyl group having from 2 to 32 carbon atoms, an alkoxycarbonyl group having from 1 to 32 carbon atoms or an aryloxycarbonyl group each of which may be substituted with a substituent selected from an alkoxy group, an alkoxycarbonyl group, an acylamino group, an alkylsulfamoyl group, an alkylsulfonamido group, an alkylsuccinimido group, a halogen atom, a nitro group, a carboxy group, a nitrile group, an alkyl group and an aryl group; and $R_{11}$ represents an arylcarbonyl group, an alkanoyl group having from 2 to 32 carbon atoms, an arylcarbamoyl group; an alkanecarbamoyl group having from 2 to 32 carbon atoms, an alkoxycarbonyl group having from 1 to 32 carbon atoms, an aryloxycarbonyl group, an alkanesulfonyl group having from 1 to 32 carbon atoms, an arylsulfonyl group, an aryl group or a 5-membered or 6-membered heterocyclic group each of which may be substituted with a substituent selected from the group consisting of the substituents as defined for $R_{10}$; and l represents an integer of 1 to 4.

27. A silver halide color photographic light-sensitive material as claimed in claim 4, wherein the photographic light-sensitive material contains at least one red-sensitive silver halide emulsion layer containing at least one cyan color forming coupler, at least one green-sensitive silver halide emulsion layer containing at least one magenta color forming coupler and at least one blue-sensitive silver halide emulsion layer containing at least one yellow color forming coupler.

28. A silver halide color photographic light-sensitive material as claimed in claim 27, wherein at least one of the at least one silver halide emulsion layer contains the compound represented by the formula (Ia).

29. A process for forming an image using the silver halide photographic light-sensitive material claimed in claim 28, comprising imagewise exposing and developing the silver halide photographic light-sensitive material, wherein the developing is carried out with at least one developing agent which forms upon development of silver halide an oxidation product which reacts with the compound of the formula (Ia) to release the group (I) which in turn generates the PUG anion in said at least one emulsion layer, and wherein the hetero atom through which PUG is bonded as a sulphur atom, an nitrogen atom or an oxygen atom.

* * * * *